US009487822B2

(12) United States Patent
Dube et al.

(10) Patent No.: US 9,487,822 B2
(45) Date of Patent: Nov. 8, 2016

(54) METHOD AND APPARATUS FOR DETERMINING COPY NUMBER VARIATION USING DIGITAL PCR

(75) Inventors: Simant Dube, Berkeley, CA (US); Jian Qin, Foster City, CA (US); Ramesh Ramakrishnan, San Jose, CA (US)

(73) Assignee: Fluidigm Corporation, South San Francisco, CA (US)

( * ) Notice: Subject to any disclaimer, the term of this patent is extended or adjusted under 35 U.S.C. 154(b) by 1560 days.

(21) Appl. No.: 12/170,414

(22) Filed: Jul. 9, 2008

(65) Prior Publication Data

US 2009/0239308 A1    Sep. 24, 2009

Related U.S. Application Data

(60) Provisional application No. 61/070,199, filed on Mar. 19, 2008.

(51) Int. Cl.

| G01N 33/483 | (2006.01) |
|---|---|
| C12Q 1/68 | (2006.01) |
| G01N 33/00 | (2006.01) |
| B01L 3/00 | (2006.01) |
| G01N 35/00 | (2006.01) |

(52) U.S. Cl.
CPC ............ *C12Q 1/6837* (2013.01); *B01L 3/5027* (2013.01); *G01N 35/00594* (2013.01); *Y10T 436/143333* (2015.01)

(58) Field of Classification Search
CPC .............. B01L 3/5027; C12Q 1/6837; C12Q 2527/137; C12Q 2537/16; C12Q 2537/165; G01N 35/00594; Y10T 436/143333
USPC .......................................... 435/288.7; 436/94
See application file for complete search history.

(56) References Cited

U.S. PATENT DOCUMENTS

| 2002/0039740 A1* | 4/2002 | Ramm et al. ..................... 435/6 |
| 2005/0252773 A1* | 11/2005 | McBride ............. G01N 27/453 |
| | | 204/450 |

OTHER PUBLICATIONS

Spurgeon, S. L. High Throughput Gene Expression Measurement with Real Time PCR in a Microfluidic Dynamic Array.2008: 3:2 (1-7).*
Chen, Yidong et al. Ratio BAsed Decisions and the Quantitative Analysis of cDNA Microarray images(1997). Journal of Biomedical Optics.2:4, 364-374.*
Baer et al., "Structure and transcription of a human gene for H1 RNA, the RNA component of human RNase P," Nucleic Acids Research, 18(1):97-103 (1990).

(Continued)

*Primary Examiner* — Rebecca M Fritchman
(74) *Attorney, Agent, or Firm* — Kilpatrick Townsend & Stockton LLP

(57) ABSTRACT

A method of estimating a concentration of DNA molecules in a biological sample includes storing a number of a plurality of reaction sites in a memory and distributing the biological sample among the plurality of reaction sites. The method also includes determining a number of the plurality of reaction sites characterized by a presence of one or more of the DNA molecules and computing a portion of the plurality of reaction sites characterized by the presence of the one or more of the DNA molecules. The method further includes estimating the concentration of the DNA molecules as a function of the portion of the plurality of reaction sites and computing a confidence interval for the estimated concentration of DNA molecules.

14 Claims, 14 Drawing Sheets

(56) References Cited

OTHER PUBLICATIONS

Carter, "Methods and strategies for analyzing copy number variation using DNA microarrays," Nature Genetics 39, S16-S21 (2007).

Emery et al., "Real-time reverse transcription-polymerase chain reaction assay for SARS-associated coronavirus," Emerg Infect Dis., 10(2):311-316 (Feb. 2004).

Fieller, "Some Problems in Interval Estimation," Journal of the Royal Statistical Society. Series B (Methodological), 16(2):175-185 (1954).

Fieller, "The distribution of the index in a normal bivariate population," Biometrika; 24(3/4):428-344 (1932).

Iafrate et al., "Detection of large-scale variation in the human genome," Nature Genetics, 36(9):949-951 (2004).

Lo et al., "Digital PCR for the molecular detection of fetal chromosomal aneuploidy," PNAS, 104(32):13116-13121 (Aug. 7, 2007).

Lupski, "Genomic rearrangements and sporadic disease," Nature Genetics 39:S43-S47, (2007).

Motulsky, *Intuitive Biostatistics*, Oxford University Press, Sep. 1995, pp. 9-60. [Chapter 1 particularly relevant].

Redon et al., "Global variation in copy number in the human genome," Nature 444:444-454 (Nov. 23, 2006)|.

Ropers et al., "New perspectives for the elucidation of genetic disorders," The American Joumal of Human Genetics, 81(2):199-207 (Aug. 1, 2007).

Sebat et al., "Large-scale copy number polymorphism in the human genome," Science 305:525-528 (Jul. 2004).

Sindelka et al., "Intracellular expression profiles measured by real-time PCR tomography in the Xenopus laevis oocyte," Nucleic Acids Research 2008 36(2):387-392.

Spurgeon et al.,"High Throughput Gene Expression Measurement with Real Time PCR in a Microfluidic Dynamic Array," PLoS One, 2008; 3(2): e1662. 7 pages total.

Vogelstein et al., "Digital PCR," Proc. Natl. Acad. Sci., Aug. 1999; 96(16): 9236-9241.

Von Luxburg, "A Geometric Approach to Confidence Sets for Ratios: Fieller's Theorem, Generalizations, and Bootstrap," Max Planck Institute for Biological Cybernetics, 2004, 24 pages.

Von Luxburg, "Confidence sets for ratios: A purely geometric approach to Fieller's theorem," Technical Report 133, Max Planck Institute for Biological Cybernetics, 2004.

Warren et al., "The Digital Array Response Curve" Mar. 8, 2007, Department of Bioengineering, Stanford University and HHMI, 20 pages total.

Wong et al., "A comprehensive analysis of common copy—number variations in the human genome," Am J Hum Genet., 80(1):91-104 (Jan. 2007).

Wu et al. in "MEMS Flow Sensors for Nano-fluidic Applications", Sensors and Actuators A 89 152-158 (2001).

Zhu et al., "High-sensitivity capillary electrophoresis of double-stranded DNA fragments using monomeric and dimeric fluorescent intercalating dyes," Anal. Chem. 66:1941-1948 (1994).

\* cited by examiner

Population Parameters:
- $\lambda$, true DNA concentration
- $p$, the probability of a hit

US 9,487,822 B2

METHOD AND APPARATUS FOR DETERMINING COPY NUMBER VARIATION USING DIGITAL PCR

CROSS-REFERENCES TO RELATED APPLICATIONS

The present application claims benefit under 35 U.S.C. §119(e) of U.S. Provisional Patent Application No. 61/070,199, filed on Mar. 19, 2008, entitled "Mathematical Analysis of Copy Number Variation on Digital Array," the disclosure of which is hereby incorporated by reference in its entirety for all purposes.

BACKGROUND OF THE INVENTION

The present invention relates generally to nanofluidic techniques. In particular, the invention provides a method and system for computing copy number variation in a DNA sample using digital PCR. More particularly, the present method and system partitions a DNA sample into a number of separate reaction chambers present in a nanofluidic chip forming a digital array. Merely by way of example, the nanofluidic methods and systems described herein are used to determine accurate estimates for concentrations of target gene and reference gene molecules in a biological sample as well as ratios of the determined concentrations. Although the techniques for nanofluidic systems are applied to digital PCR using digital arrays, it would be recognized that the invention has a much broader range of applicability.

Some conventional digital polymerase chain reaction (PCR) techniques utilize sequential limiting dilutions of target DNA followed by amplification using PCR. Using this digital PCR technique, it is possible to quantitate single DNA target molecules. Another digital PCR technique utilizes a microfluidic biochip in which DNA molecules are partitioned rather than diluted. As an example, the microfluidic biochip typically utilizes integrated channels and valves that partition mixtures of sample and reagents into reaction chambers having nanoliter volumes. DNA molecules in each mixture are randomly partitioned into the various chambers of the biochip, the chip is thermocycled, and the chip is imaged to determine the number of reaction chambers having a desired DNA molecule.

Copy number variation (CNV) is the gain or loss of genomic regions which range from 500 bases on upwards in size. Whole genome studies have revealed the presence of large numbers of CNV regions in human DNA and a broad range of genetic diversity among the general population. Copy number variations have been the focus of a number of recent studies as a result of their role in human genetic disorders.

Current whole-genome scanning technologies use array-based platforms (array-CGH and high-density SNP microarrays) to study CNVs. These approaches are characterized by high throughput, but lack resolution and sensitivity. Real-time PCR is a sequence-specific technique that is easy to perform, but is limited in its discriminating power beyond a 2-fold difference. CNV determination using a digital array is based upon the ability to partition DNA sequences. Given the number of molecules per panel and the dilution factor, the concentration of the target sequence in a DNA sample can be accurately calculated.

In a multiplex PCR reaction with 2 or more assays, multiple genes can be quantitated simultaneously and independently, effectively eliminating any pipetting errors if separate reactions have to be set up for different genes. When a single copy reference gene (e.g., RNase P) is used in the reaction, the ratio of the target gene to the reference gene would reflect the copy number per haploid genome of the target gene.

DNA quantitation in the digital array is based on the partitioning of a PCR reaction into an array of several hundreds or even a few thousands of reaction chambers or wells. If a DNA sample only includes several DNA molecules of interest in the sample, most of the reaction chambers in a digital PCR chip will include either one or no molecules. Thus, to first order, the number of positive reaction chambers at the PCR end-point provides a count of the molecules of interest in the sample. However, if the number of molecules of interest is large compared to the number of reaction chambers, it is likely that a number of the reaction chambers will include more than one molecule of interest and the positive reaction chamber count will be significantly less than the number of molecules of interest. Thus, there is a need in the art for improved methods and systems for estimating the number of molecules in a DNA sample.

SUMMARY OF THE INVENTION

According to the present invention, techniques for nanofluidic systems are provided. In particular, the invention provides a method and system for computing copy number variation in a DNA sample using digital PCR. More particularly, the present method and system partitions a DNA sample into a number of separate reaction chambers present in a nanofluidic chip forming a digital array. Merely by way of example, the nanofluidic methods and systems described herein are used to determine accurate estimates for concentrations of target gene and reference gene molecules in a biological sample as well as ratios of the determined concentrations. Although the techniques for nanofluidic systems are applied to digital PCR using digital arrays, it would be recognized that the invention has a much broader range of applicability.

According to an embodiment of the present invention, a method of estimating a concentration of DNA molecules in a biological sample is provided. The method includes storing a number of a plurality of reaction sites in a memory and distributing the biological sample among the plurality of reaction sites. The method also includes determining a number of the plurality of reaction sites characterized by a presence of one or more of the DNA molecules and computing a portion of the plurality of reaction sites characterized by the presence of the one or more of the DNA molecules. The method further includes estimating the concentration of the DNA molecules as a function of the portion of the plurality of reaction sites and computing a confidence interval for the estimated concentration of DNA molecules.

According to another embodiment of the present invention, a method of estimating a concentration of a DNA molecule in a biological sample is provided. The method includes storing a number of a plurality of reaction sites in a memory, distributing the biological sample among the plurality of reaction sites, determining a number of the plurality of reaction sites characterized by a presence of one or more of the DNA molecules, computing a portion of the plurality of reaction sites characterized by the presence of the one or more of the DNA molecules, and computing a standard deviation as a function of the portion of the plurality of reaction sites characterized by the presence of the one or more of the DNA molecules. The method also includes forming a first probability density function having a mean based on the portion of the plurality of reaction sites characterized by the presence of the one or more of the DNA molecules and the standard deviation, defining a first limit and a second limit, and computing a first confidence interval associated with an area under the first probability density function between the first limit and the second limit. The method further includes forming a second probability density function as a function of a set of concentration values. Forming a second probability density function includes computing a hit percentage as a function of a concentration value of the set of concentration values, computing a second probability density function value as a function of the first probability density function evaluated at the hit percentage, and repeating computing a first hit percentage and computing a second probability density function for the set of concentration values. Moreover, the method includes defining a third limit and a fourth limit and computing a second confidence interval associated with an area under the second probability density function between the third limit and the fourth limit.

According to a particular embodiment of the present invention, a method of estimating a ratio of a concentration of a first DNA molecule in a biological sample to a concentration of a second DNA molecule in the biological sample is provided. The method includes storing a number of a plurality of reaction sites in a memory and distributing the biological sample among the plurality of reaction sites. The method also includes determining a first number of the plurality of reaction sites characterized by a presence of one or more of the first DNA molecules and determining a second number of the plurality of reaction sites characterized by a presence of one or more of the second DNA molecules. The method further includes computing a first portion of the plurality of reaction sites characterized by the presence of the one or more first DNA molecules and computing a portion of the plurality of reaction sites characterized by the presence of the one or more second DNA molecules. Moreover, the method includes estimating the concentration of the first DNA molecule as a function of the first portion of the plurality of reaction sites, estimating the concentration of the second DNA molecule as a function of the second portion of the plurality of reaction sites, and computing the ratio of the concentration of the first DNA molecule in the biological sample to the concentration of a second DNA molecule in the biological sample.

According to another particular embodiment of the present invention, a method of estimating a ratio of a concentration of a first DNA molecule in a biological sample to a concentration of a second DNA molecule in the biological sample is provided. The method includes storing a number of analysis panels in a memory, storing a number of a plurality of reaction sites per analysis panel in the memory, and distributing the biological sample among the plurality of reaction sites of the analysis panels. The method also includes forming a first histogram of the concentration of the first DNA molecule per panel based on the number of analysis panels and forming a second histogram of the concentration of the second DNA molecule per panel based on the number of analysis panels. The method further includes forming a ratio histogram. Forming the ratio histogram includes defining a bin extent associated with the ratio histogram and determining a number of ratio pairs from the first histogram and the second histogram, respectively, falling within the bin extent, thereby defining a value associated with the first histogram and a value associated with the second histogram. Forming a ratio histogram also includes computing a product of the first histogram evaluated at the value associated with the first histogram and the second histogram evaluated at the value associated with the second histogram, storing a histogram entry for the product in the memory associated with the bin extent, and repeating determining a number of ratio pairs, computing a product, and storing a histogram entry to form the ratio histogram.

According to a specific embodiment of the present invention, a system for estimating a concentration of a DNA molecule in a biological sample is provided. The system includes a light source, a first optical system in optical communication with the light source, and a nanofluidic chip support configured to receive a nanofluidic chip having a plurality of reaction chambers. Optical radiation from the light source is directed onto the nanofluidic chip by the first optical system. The system also includes a second optical system configured to receive optical radiation emitted from the nanofluidic chip, a detector in optical communication with the second optical system, and a computer comprising a data processor and a computer-readable medium storing a plurality of instructions for controlling a data processor to estimate the concentration of the DNA molecule in the biological sample. The plurality of instructions includes instructions that cause the data processor to determine a number of the plurality of reaction chambers characterized by a presence of one or more of the DNA molecules and instructions that cause the data processor to compute a portion of the plurality of reaction sites characterized by the presence of the one or more of the DNA molecules. The plurality of instructions also includes instructions that cause the data processor to estimate the concentration of the DNA molecules as a function of the portion of the plurality of reaction sites and instructions that cause the data processor to compute a confidence interval for the estimated concentration of DNA molecules.

Embodiments of the present invention provide methods and systems in which a digital array provides a robust and easy-to-use platform to study CNVs. Utilizing embodiments of the present invention, the true concentration of molecules from the observed positive reactions in a panel can be estimated along with associated confidence intervals. Additionally, the methods and systems described herein provide for the computation of the ratio of two concentrations in a CNV experiment using the digital array with multiplex PCR.

Numerous benefits are achieved using the present invention over conventional techniques. For example, some embodiments provide methods and systems to distinguish between DNA samples with different copy number variations with greater resolution than using conventional techniques. Additionally, embodiments of the present invention provide for more convenient laboratory systems. These and other benefits have been described throughout the present specification and more particularly below. Various additional objects, features, and advantages of the present invention can be more fully appreciated with reference to the detailed description and accompanying drawings that follow.

DETAILED DESCRIPTION OF SPECIFIC EMBODIMENTS

Figure 1:
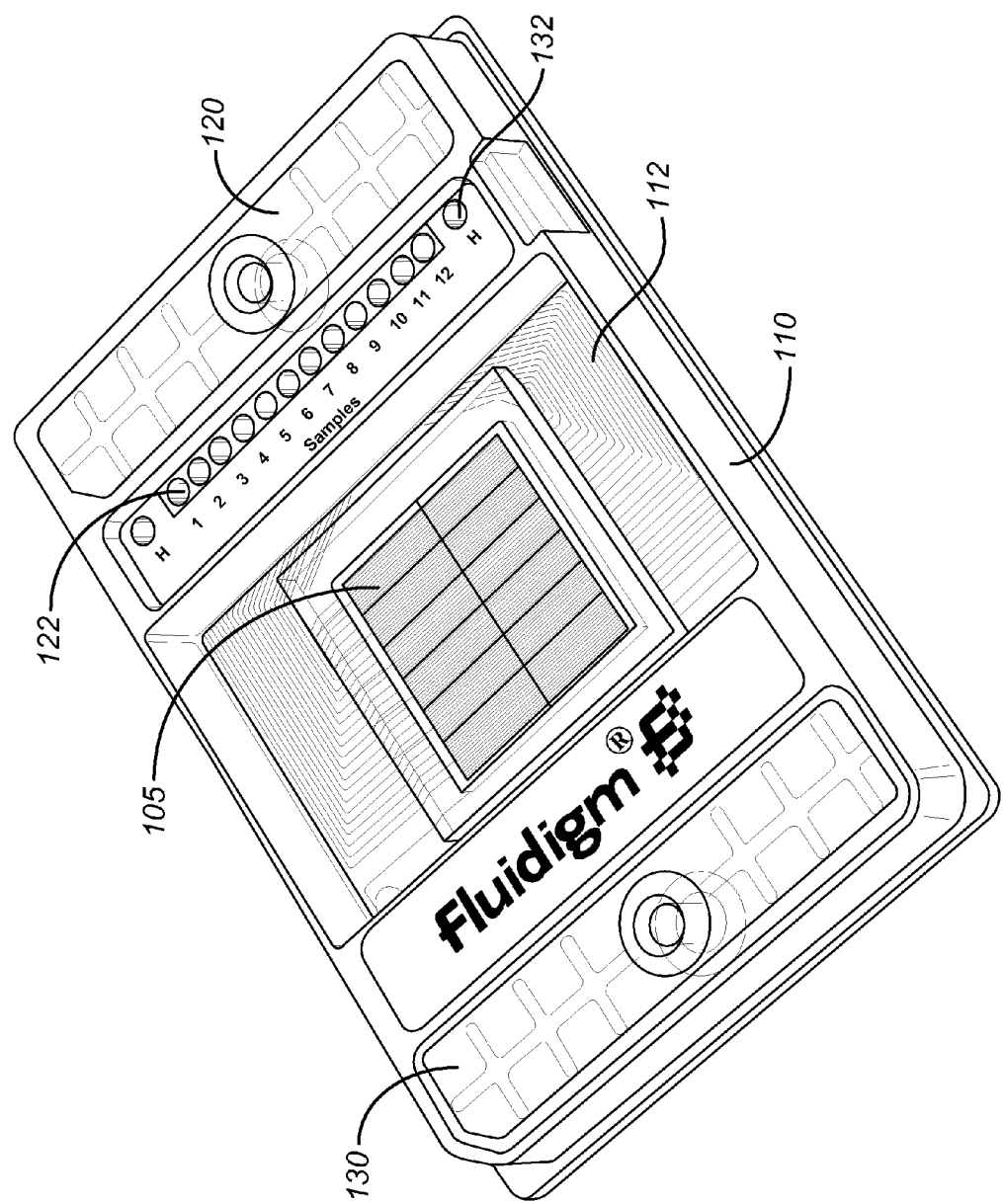
FIG. 1 is a simplified diagram of a nanofluidic biochip according to an embodiment of the present invention.

The conventional view in human genetics held that genes were always present in two copies per diploid cell. After the completion of the human genome project about five years ago, it is now clear that some genes are present in multiple copies in different individuals, and that occasionally huge regions of the genome are duplicated or deleted. Such copy number variation (CNV) is now known to be associated with many human diseases. Copy number variations (CNVs) can be determined using a technique known as Digital PCR in which DNA samples are quantitated using limiting dilutions. Another technique, rather than using limiting dilutions, utilizes a nanofluidic chip called a digital array, which partitions individual DNA molecules in separate reaction chambers. The digital array chip utilizes integrated channels and valves that partition mixtures of sample and reagents into, for example, 765 reaction chambers, each with volumes on the scale of nanoliters.

When the concentration of the input target molecules is large, an individual reaction chamber could have multiple molecules present in the reaction chamber. Embodiments of the present invention provide methods and systems, which are mathematically sound and computationally efficient, to accurately analyze CNV in a DNA sample. These methods and systems are applicable to the technology of the digital array as well as other DNA analysis techniques. Furthermore, embodiments of the present invention provide methods and systems to accurately estimate the true concentration of the molecules in the DNA sample and then determine the ratios of different sequences along with statistical confidence intervals on these estimations. Some embodiments of the present invention utilize theories of statistics and probability whereas other embodiments utilize numerical algorithms and formulas that provide close approximations for the true concentration of molecules in a DNA sample.

The digital array provides a robust and easy-to-use platform to study CNVs. Embodiments of the present invention utilize a mathematical framework to calculate the true concentration of molecules from the observed positive reactions in a panel. Additionally, embodiments provide methods and systems to perform statistical analysis to find predetermined (e.g., 95%) confidence intervals of the true concentrations as well as the ratio of two concentrations (e.g., a target gene and a reference gene) in a CNV experiment using the digital array with multiplex PCR.

The copy number variation problem can be stated as follows: Given two counts $H_1$ and $H_2$ of positive chambers for two genes in a digital array panel, how can one estimate a ratio of true concentrations $r=\lambda_1/\lambda_2$ of the two genes and a confidence interval $[r_{Low}, r_{High}]$ on the estimation?

Methods and systems related to determining CNV using digital PCR are discussed in copending and commonly assigned U.S. Provisional Patent Application No. 60/967,897, filed on Sep. 7, 2007 and entitled "Copy Number Variation Determination by Digital PCR," the disclosure of which is hereby incorporated by reference in its entirety for all purposes. Some embodiments of the present invention decompose the CNV problem into two parts:

1. Given a count H of positive chambers, how can one estimate the true concentration $\lambda$ of target molecules in the DNA sample and a confidence interval $[\lambda_{Low}, \lambda_{High}]$ on this estimation?

2. Given estimated true concentrations $\lambda_1$ and $\lambda_2$ of the reference gene and the target gene in the DNA sample, respectively, and their respective confidence intervals $[\lambda_{1,Low}, \lambda_{1,High}]$ and $[\lambda_{2,Low}, \lambda_{2,High}]$, how can one estimate the ratio $r=\lambda_1/\lambda_2$ and a confidence interval $[r_{Low}, r_{High}]$ on this estimation?

It should be noted that embodiments of the present invention differ from recent approaches to quantitation in digital arrays. In a preprint entitled "The Digital Array Response Curve" (http://thebigone.stanford.edu/quake/publications/DigResCurve.pdf), by Luigi A. Warren et al., a Bayesian approach is utilized in which given the number of positive chambers in a panel, one computes the number of molecules for this particular experiment. In the Bayesian approach, one assumes some prior probability distribution on the number of molecules and builds a probability distribution of getting the observed number of positive chambers for each possible number of molecules. In the preprint by Warren et al., a uniform distribution of number of molecules was assumed, with a maximum number assumed to be 4000, and using Bayesian and combinatorial methods, the digital PCR response curve was calculated. Embodiments of the present invention differ from the Bayesian approach described above since they provide methods and systems that estimate the true concentration of molecules in the DNA sample, as if this experiment were to be repeated infinitely many times.

FIG. 1 is a simplified diagram of a nanofluidic biochip according to an embodiment of the present invention. As illustrated in FIG. 1, the nanofluidic biochip, also referred to as a digital array, includes a carrier 110, which may be made from materials providing suitable mechanical support for the various elements of the nanofluidic biochip. As an example, the biochip is made using an elastomeric polymer. The outer portion of the biochip has the same footprint as a standard 384-well microplate and enables stand-alone valve operation. As described below, there are 12 input ports corresponding to 12 separate sample inputs to the chip. The biochip has 12 panels 105 and each of the 12 panels contains 765 6 nl reaction chambers with a total volume of 4.59 µl per panel. Microfluidic channels 112 connect the various reaction chambers on the panels to fluid sources as described more fully below.

Pressure is applied to accumulator 120 in order to open and close valves connecting the reaction chambers to fluid sources. As illustrated in FIG. 1, 12 inlets 122 are provided for loading of the sample reagent mixture. 48 inlets 122 are used in some applications to provide a source for reagents, which are supplied to the biochip when pressure is applied to accumulator 120. In applications in which reagents are not utilized, inlets 122 and reagent side accumulator 120 may not be used. Additionally, two inlets 132 are provided in the embodiment illustrated in FIG. 1 to provide hydration to the biochip. Hydration inlets 132 are in fluid communication with the biochip to facilitate the control of humidity associated with the reaction chambers. As will be understood to one of skill in the art, some elastomeric materials utilized in the fabrication of the biochip are gas permeable, allowing evaporated gases or vapor from the reaction chambers to pass through the elastomeric material into the surrounding atmosphere. In a particular embodiment, fluid lines located at peripheral portions of the biochip provide a shield of hydration liquid, for example, a buffer or master mix, at peripheral portions of the biochip surrounding the panels of reaction chambers, thus reducing or preventing evaporation of liquids present in the reaction chambers. Thus, humidity at peripheral portions of the biochip can be increased by adding a volatile liquid, for example water, to hydration inlets 132. In a specific embodiment, a first inlet is in fluid communication with the hydration fluid lines surrounding the panels on a first side of the biochip and the second inlet is in fluid communication with the hydration fluid lines surrounding the panels on the other side of the biochip.

Although the nanofluidic biochip illustrated in FIG. 1 includes 12 panels, each having 765 reaction chambers with a volume of 6 nl per reaction chamber, this is not required by the present invention. The particular geometry of the digital array will depend on the particular applications. Thus, the scope of the present invention is not limited to digital arrays with 12 panels having 765 reaction chambers, but other combinations are included within the scope of the present invention. One of ordinary skill in the art would recognize many variations, modifications, and alternatives. Additional description related to digital arrays suitable for use in embodiments of the present invention are provided in U.S. Patent Application Publication No. 2005/0252773 (U.S. patent application Ser. No. 11/084,357), which is commonly assigned and hereby incorporated by reference for all purposes.

Running large numbers of replicate samples can require significant quantities of reagents. In an embodiment of the present invention, digital PCR is conducted in microvolumes. The reaction chambers for running low volume PCR may be from about 2 nL to about 500 nL. The lower the reaction chamber volume, the more the number of individual assays that may be run (either using different probe and primer sets or as replicates of the same probe and primer sets or any permutation of numbers of replicates and numbers of different assays). In one embodiment, the reaction chamber is from about 2 nL to about 50 nL, preferably 2 nL to about 25 nL, more preferably from about 4 nL to about 15 nL. In some embodiments, the reaction chamber volume is about 4 nL, about 5 nL, about 6, nL, about 7 nL, about 8, nL, about 9 nL, about 10 nL, about 11 nL, or about 12, nL. The sample chambers may be constructed of glass, plastic, silicon, elastomeric polymers such as polydimethylsiloxane, polyurethane, or other polymers. The samples processed by the method of the invention are well suited for use in variable copy number analysis using the BioMark™ system (Fluidigm Corporation, South San Francisco, Calif.). The BioMark™ system uses a polydimethylsiloxane microfluidic device that provides for running multiple assays on multiple samples.

The Fluidigm nanofluidic chips (digital arrays) and BioMark™ fluorescence imaging thermal cycler system, are manufactured by Fluidigm Corporation (South San Francisco, Calif.). Chips are fabricated following the Multilayer Soft Lithography (MSL) methodology (Unger M A, Chou H P, Thorsen T, Scherer A, Quake S R, Monolithic microfabricated valves and pumps by multilayer soft lithography, Science 2000; 288:113-116). The chip has sample channels that have 10 µm average semi-elliptical depth, 70 µm width, with parallel spacing 200 µm on-center. Sample fluidics are fabricated with a two-layer mold process to create partition chambers 265 µm (depth)×150 µm×150 µm arranged along each sample channel. On a separate silicone layer, the control channels of the chip run perpendicular to the sample channels. The intersections of the channels form deflective valves for routing fluids. Upon pressurization of the control channels, a thin membrane between layers closes off the sample channels to isolate individual partition chambers. The control channels are 15 µm deep, 50 µm wide with parallel spacing 300 µm on center.

PCR mixes are loaded into each panel and single DNA molecules are randomly partitioned into the various reaction chambers. After loading of the panels and reaction chambers, the digital array is thermocycled and then imaged on an appropriate reader, for example, a BioMark™ instrument available from the present assignee. The data produced is analyzed using Digital PCR Analysis software available from the present assignee or other suitable analysis software.

Figure 2A:
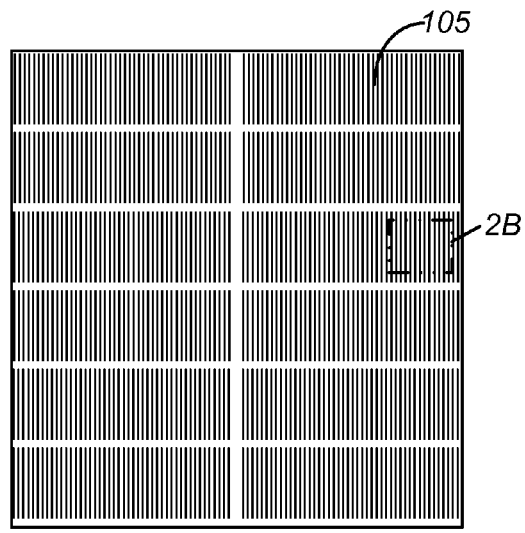
FIGS. 2A-2D are simplified diagrams of portion of the nanofluidic biochip illustrated in FIG. 1.
Figure 2B:
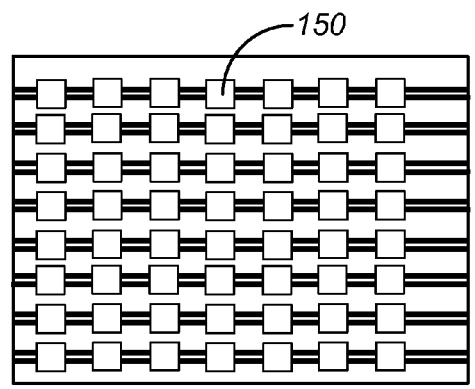
Figure 2C:
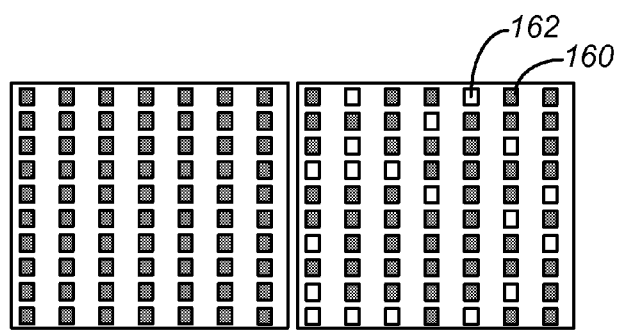
Figure 2D:
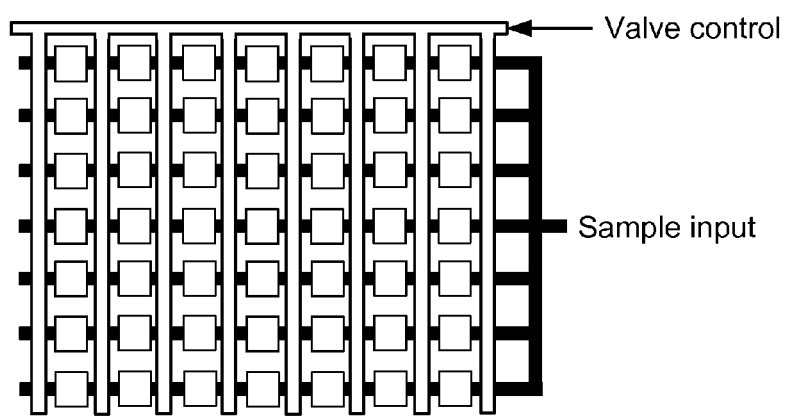

FIGS. 2A-2D are simplified diagrams of portion of the nanofluidic biochip illustrated in FIG. 1. FIG. 2A illustrates the 12 panels 105, each of the panels including a number of reaction chambers. FIG. 2B illustrates the geometry of a number of reaction chambers 150 contained in a panel. The reaction chambers 150 are spaced on 200 µm centers as illustrated. FIG. 2B illustrates a fluorescence image of a portion of a panel. The left side of the illustration is a control section, with all the reaction chambers illustrated as dark. The right side of the illustration shows how in a typical experiment, many of the reaction chambers are dark 160, generating no significant fluorescent emission. However, a portion of the reaction chambers have fluorescent emission, indicating a "positive" reaction chamber 162. As illustrated in FIG. 2D, sample channels run left to right connecting individual reaction chambers and control channels run top to bottom in the lower layer. Upon pressurization of the control channels, a thin membrane between layers closes off the sample channels to isolate individual reaction chambers. The valves partition individual chambers that are kept closed during the PCR experiment.

In some embodiments, a variety of devices and methods for conducting microfluidic analyses are utilized herein, including devices that can be utilized to conduct thermal cycling reactions such as nucleic acid amplification reactions. The devices differ from conventional microfluidic devices in that they include elastomeric components; in some instances, much or all of the device is composed of elastomeric material. For example, amplification reactions can be linear amplifications, (amplifications with a single primer), as well as exponential amplifications (i.e., amplifications conducted with a forward and reverse primer set).

The methods and systems provided by some embodiments of the present invention utilize blind channel type devices in performing nucleic acid amplification reactions. In these devices, the reagents that are typically deposited within the reaction sites are those reagents necessary to perform the desired type of amplification reaction. Usually this means that some or all of the following are deposited: primers, polymerase, nucleotides, metal ions, buffer, and cofactors, for example. The sample introduced into the reaction site in such cases is the nucleic acid template. Alternatively, however, the template can be deposited and the amplification reagents flowed into the reaction sites. As discussed in more detail throughout the present specification, when a matrix device is utilized to conduct an amplification reaction, samples containing nucleic acid template are flowed through the vertical flow channels and the amplification reagents through the horizontal flow channels or vice versa.

An embodiment of the present invention has been applied to estimating the true concentration of the molecules in the DNA sample from which we extracted 6 nl×765=4.59 µl of sample was extracted for each panel. Consider the universe of an infinite number of digital array chambers filled with an infinite amount of the DNA sample, where the true concentration of the target molecules per chamber (e.g., reaction chamber volume of 6 nl) is represented by $\lambda$. The true concentration is an unknown population parameter of this infinite DNA sample. If, after the reaction chamber filling process, no molecule is present in the chamber, then it constitutes failure in the sense of a Bernoulli experiment. If the chamber includes one or more molecules, that is, if it gets a "hit" and is therefore positive, then it constitutes success. Let the probability of success (i.e., one or more molecules per chamber) be p, which is an unknown parameter of the experiment.

A fundamental insight of the present inventors is that one can first estimate p and then estimate $\lambda$, as the two parameters are interrelated. Another important insight is that a digital array panel is a finite random statistical sampling of the underlying infinite universe of reaction chambers.

The inventors have noted that embodiments of the present invention are related to a case in which one is trying to estimate the true mean height µ of an infinite population of people and randomly selects N people and uses the mean height m of this finite sample as an unbiased estimator of the population mean. If the standard deviation of height in the population is $\sigma$, then X denoting the random variable of the sample mean has a sampling distribution F(X) with mean µ and standard deviation $$s = \frac{\sigma}{\sqrt{N}},$$

the latter often referred as the standard error of the mean. The sampling distribution is the probability distribution of the sample statistic. From the Central Limit Theorem, it is known that the sampling distribution can be approximated by a normal distribution as N gets large. From the sampling distribution F, one can compute the 95% confidence interval by computing the 95% area under the distribution, which is approximately $m \pm z_c s$, where $z_c=1.96$, assuming a normal distribution for large values of N. The meaning of the 95% confidence interval is that if one were to repeat this sampling process many times, then 95% of the time, the population mean height will lie within the specified confidence intervals.

Figure 3:
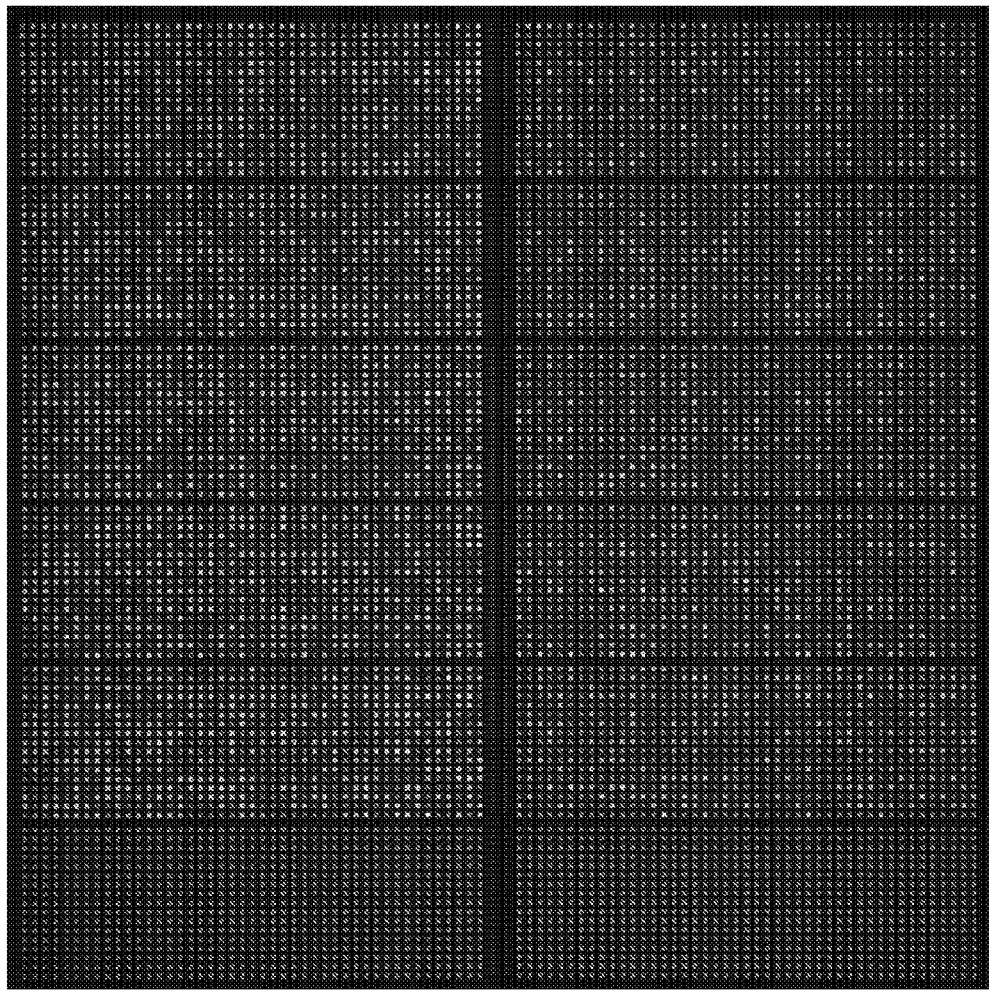
FIG. 3 is an image of fluorescent emissions from a digital array according to an embodiment of the present invention.

FIG. 3 is an image of fluorescent emissions from a digital array according to an embodiment of the present invention. As illustrated in FIG. 3, human genomic DNA NA10860 was quantitated in the left five panels and the RPP30 synthetic construct was quantitated in the right 5 panels. The total volume of the PCR mix in each panel was 6 nl×765 reaction chambers=4.59 µl). Both NA10860 and RPP30 were quantitated using the RPP30 (FAM) assay in the digital array illustrated in FIG. 3. The two bottom panels are referred to as no template control (NTC). The positive chambers that originally contained one or more DNA molecules are characterized by fluorescence in FIG. 3 and can be counted by digital array analysis software.

As described more fully throughout the present specification, the chip was thermocycled and imaged on the BioMark™ real-time PCR system available from the present assignee and Digital PCR Analysis software, such as the BioMark™ Digital PCR Analysis available from the present assignee, was used to count the number of positive chambers in each panel. When two assays with two fluorescent dyes are used in a multiplex digital PCR reaction, two genes can be independently quantitated. This ability to independently quantitate genes is used as described herein to study copy number variations using the digital array.

In order to estimate p, let the number of chambers in the panel be C and let the number of positive chambers in the panel be H. Consider $$P = \frac{H}{C}$$

as an estimator of p. The inventors have determined that P is an unbiased estimator of p and its sampling distribution F has expectation p and standard deviation $$\sqrt{\frac{p(p-1)}{C}}.$$

As illustrated in FIG. 9, if one considers an infinite universe of chambers, a digital array panel is a finite sampling of this universe. The positive chambers, which have hits of one or more molecule, are shown as filled squares in the universe and the panel, which may have 765 reaction chambers.

If one defines independent random variables:

$$X_i = \begin{cases} 0, & \text{if } i\text{-}th \text{ chamber is negative} \\ 1, & \text{if } i\text{-}th \text{ chamber is positive} \end{cases}$$

These variables are independent in the same way tosses of a coin are independent of each other. It can be shown that $E(X_i)$ is p and $Var(X_i)$ is $p(1-p)$, where E and Var are expectation and variance, respectively.

Now, consider the random variable:

$$Y = \frac{1}{C}\sum_{i=1}^{C} X_i$$

Note that the random variable of the proposed estimator $$P = \frac{H}{C}$$

is the same as Y, and it can be shown that $E(Y)$ is p and $Var(Y)$ is $$\frac{p(p-1)}{C}.$$

To see why the latter is true, note that $Var(\alpha X)$ is $\alpha^2 Var(X)$ and for independent variables $Var(X_1+X_2)=Var(X_1)+Var(X_2)$.

From the Central Limit Theorem, the sampling distribution of Y can be approximated by a normal distribution as C gets large. As described below, in the estimation of $F(Y)$, the standard deviation is $$\sqrt{\frac{p(p-1)}{C}},$$

in which p is unknown. If C is large enough, then P can be used as an estimation of p. For estimating the confidence limits at the level of confidence determined by $z_c$ note that at the confidence limits we have $$P - p = \pm z_c \sqrt{\frac{p(1-p)}{C}}.$$

By squaring both sides and solving the resulting quadratic equation for p in terms of P, one can show that if C is large enough, then the confidence limits are given by:

$$P_{High,Low} = P \pm z_c \sqrt{\frac{P(1-P)}{C}}.$$

The inventors have determined for that a digital array with panels having 765 reaction chambers, C is an integral multiple of 765 and is large enough for the above approximation to hold. Thus, in some embodiments, P is used as an estimation of p.

To estimate $\lambda$, the relationship between p and $\lambda$ is established. The inventors have noted that if M is the expected number of molecules in C chambers, then $M=\lambda C$. Since the probability of getting no molecules in any chamber is the product of probabilities of none of M molecules being in that chamber, we have:

$$1 - p = \lim_{C \to \infty}\left(1 - \frac{1}{C}\right)^M = \lim_{C \to \infty}\left(1 - \frac{\lambda}{\lambda C}\right)^M = \lim_{M \to \infty}\left(1 - \frac{\lambda}{M}\right)^M = e^{-\lambda}.$$

The inventors have determined that this result shows that the Binomial distribution approaches the Poisson distribution as the number of Bernoulli trials gets arbitrarily large. Therefore, $$\lambda = -\ln(1-p),$$

which establishes the relationship between $\lambda$ and p.

Figure 10A:
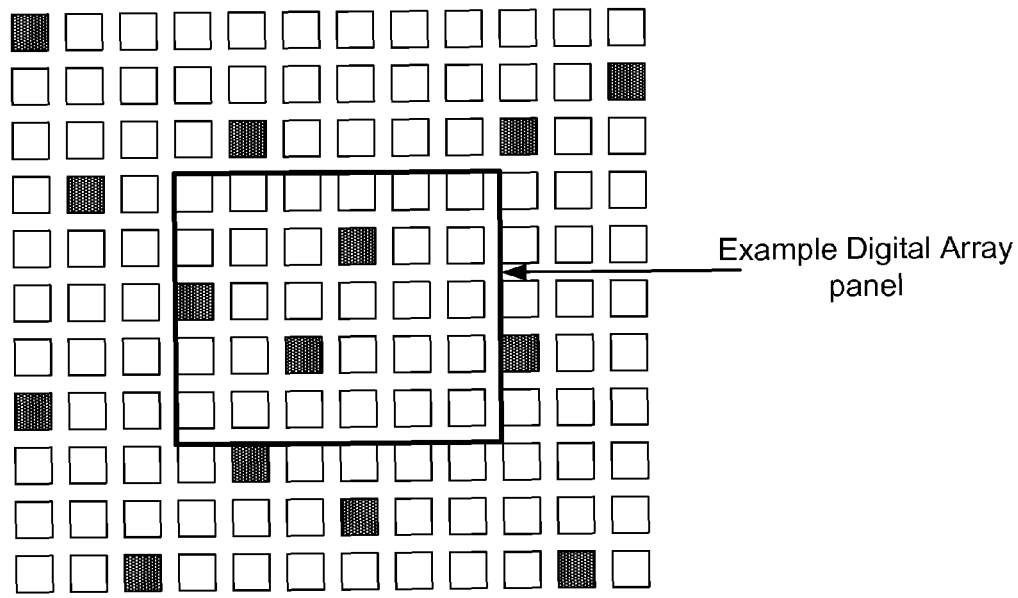
FIG. 10A is simplified diagram of a panel overlaid on a universe of reaction chambers according to an embodiment of the present invention.
Figure 10B:
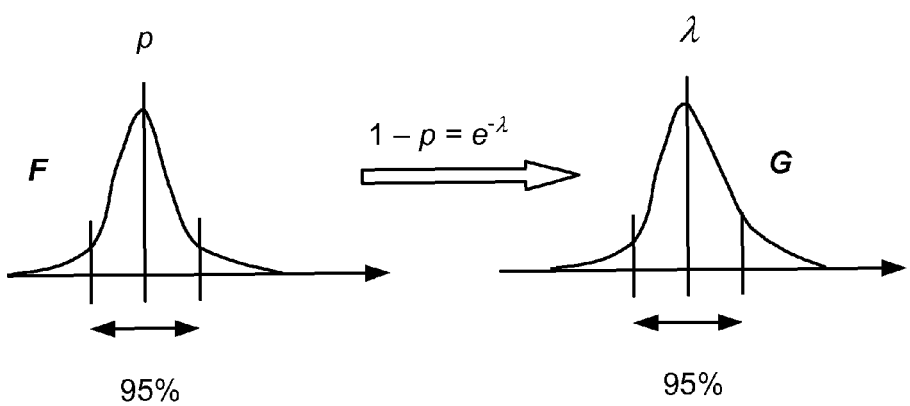
FIG. 10B is a simplified diagram illustrating how a sampling distribution of the estimated concentration is derived from a sampling distribution of the estimated hit rate according to an embodiment of the present invention.

From the sampling distribution $F(Y)$ one can get the sampling distribution of the random variable of the sample mean concentration as $$G(\Lambda) = F(Y)\frac{dY}{d\Lambda} = F(Y)(1 - Y),$$

which follows from the fact that probabilities have to be preserved for these continuous probability distributions. Note that due to nonlinear relationship between $\lambda$ and p, one cannot make assumptions about G. In general, G is not normal and $E(\Lambda) \neq -\ln(1-E(Y))$. From G, one can estimate $\lambda$ and its 95% confidence interval. FIG. 10 illustrates how from the sampling distribution of the estimation of p, one can obtain the sampling distribution of estimation of $\lambda$.

Since C is large, the standard deviation of $F(Y)$ is very small, and the transformation of Y into $\Lambda$ is approximated as a linear function, and therefore G can be assumed to be normal and therefore the 95% confidence interval $[\lambda_{Low}, \lambda_{High}]$ can be approximated as follows:

$$P_{Low,High} = P \mp 1.96\sqrt{\frac{P(1-P)}{C}},$$

$$\lambda_{Low} = -\ln(1 - P_{Low}) \text{ and}$$

$$\lambda_{High} = -\ln(1 - P_{High}).$$

Thus, utilizing embodiments of the present invention, methods and systems are provided for estimating the true concentration of a target gene in a DNA sample.

The inventors have performed computer simulations to verify that the methods and systems described herein correspond to a real-world environment. For this purpose, one can use a random number generator and a computer program to simulate the universe of the digital array chambers. If a panel has C chambers, consider a universe of C×K chambers where K is a large number chosen for simulation. The methodology is as follows: choose some value of $\lambda$ as the true concentration of molecules per chamber. Therefore, in total, there will be $\lambda \times C \times K$ molecules in the universe. Assign each of these molecules randomly to one of the various reaction chambers. Extract K panels out of this universe and for each of the panels, compute $$P = \frac{H}{C}$$

as an estimator of p and plot its histogram over all the K panels. The mean should be $p = 1 - e^{-\lambda}$ and the standard deviation should be $$\sigma = \sqrt{\frac{p(p-1)}{C}}.$$

For each of these panels, estimate λ and compute the 95% confidence interval. In 95% of the K panels, the true value of λ should lie within the confidence interval.

Figure 11:
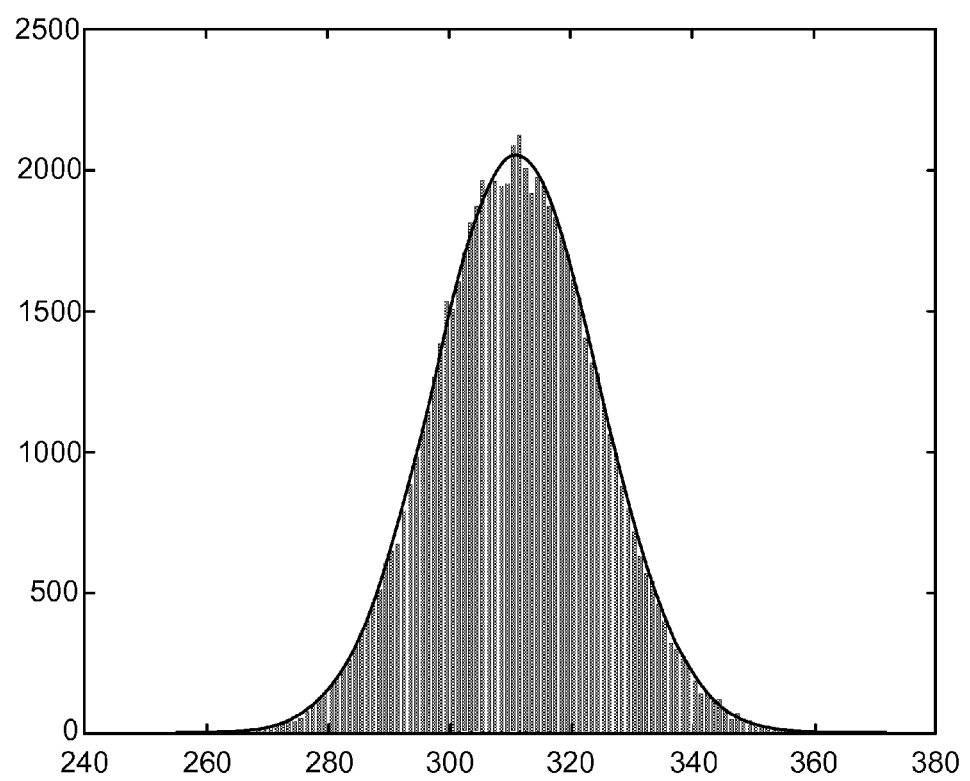
FIG. 11 is a simplified histogram illustrating a number of hits per chamber formed according to an embodiment of the present invention.

For our computer simulations we chose M=400 molecules per panel, that is, $$\lambda = \frac{400}{765}$$

molecules per chamber. We chose K=70,000. FIG. 11 illustrates a histogram of H formed according to an embodiment of the present invention. As illustrated in FIG. 11, the histogram of H is really the same as the distribution of P scaled by a factor of C (765). Table 1 illustrates a comparison between the metrics of the histogram, shown in FIG. 11, of the number of positive chambers obtained in the computer simulation and the metrics predicted by the methods and systems described herein. As illustrated by Table 1, there is a close match between the predicted values and the actual computer simulation values. In the same way, the sampling distribution of the number of molecules (illustrated by the curve in FIG. 11) matched well with that predicted by the methods and systems described herein.

TABLE 1

|  | Theoretical Predictions | Simulation Results |
| --- | --- | --- |
| Mean | 311.5 | 311.48 |
| Standard Deviation | 13.59 | 13.58 |
| Percent of times M = 400 lies in the computed 95% confidence interval | 95% | 94.44% |

Figure 4:
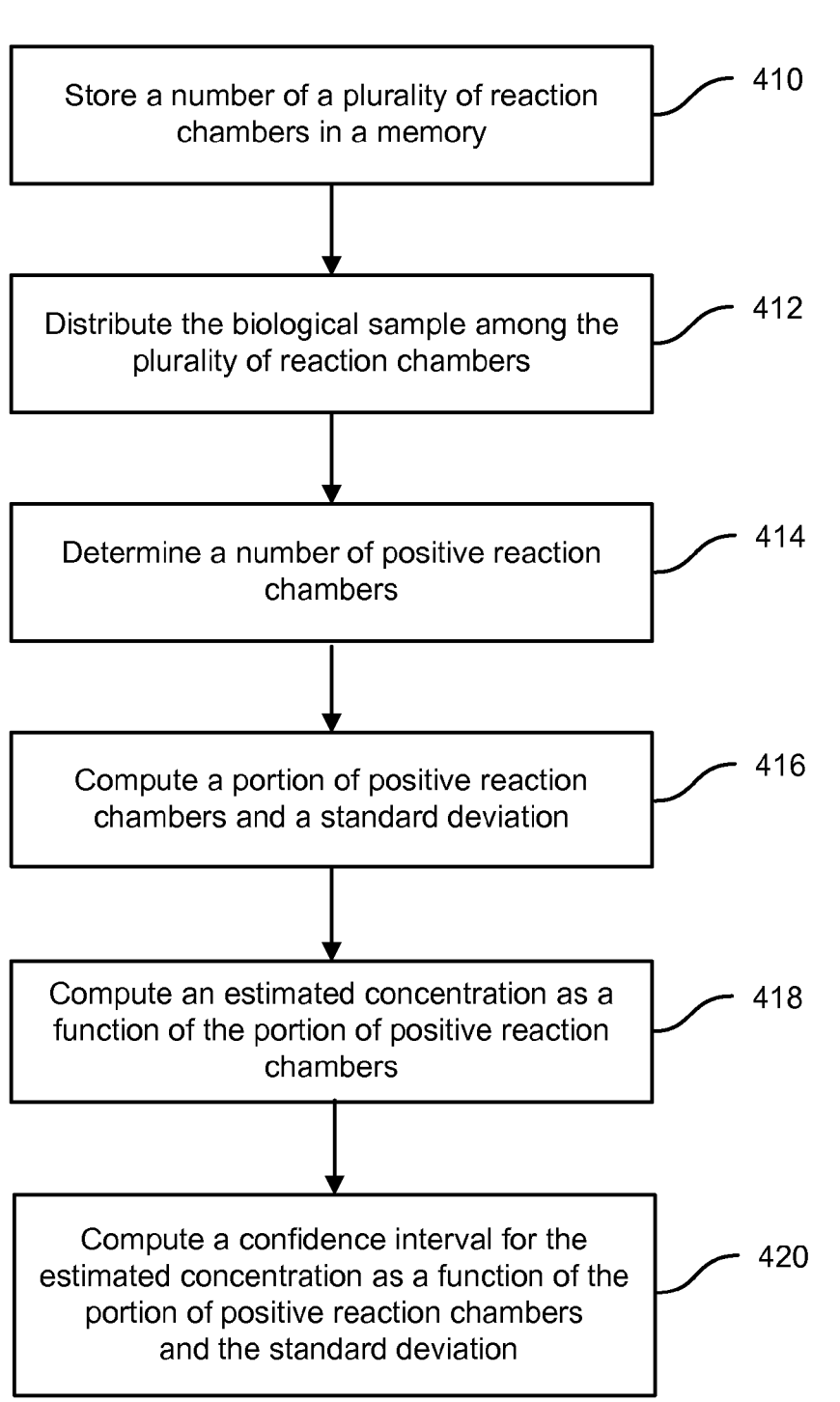
FIG. 4 is a simplified flowchart illustrating a method of determining a concentration of DNA molecules according to an embodiment of the present invention.

FIG. 4 is a simplified flowchart illustrating a method 400 of determining a concentration of DNA molecules according to an embodiment of the present invention. The method illustrated in FIG. 4 provide for approximates of the DNA molecule concentration and the confidence interval associated with the DNA molecule concentration. The number of reaction chambers in a panel is stored into a memory (410). The number of reaction chambers, for example, C=765, can be input using suitable input devices such as a keyboard of a computer system. The memory is provided as part of the sample analysis system, for example, the system illustrated in FIG. 12. The biological sample is distributed among the reaction chambers (412). In a particular embodiment, the biological sample is partitioned using a digital array to form a number of reaction chambers in which the concentration of DNA molecules is less than one per chamber. After partitioning in the digital array in this particular embodiment, the biological sample is thermocycled and imaged to determine a number of positive reaction chambers (414). In embodiments of the present invention, positive reaction chambers (denoted by the symbol H) are those reaction chambers associated with one or more DNA molecules of interest.

The portion of the reaction chambers in the panel that are positive reaction chambers is computed (e.g., P=H/C) and a standard deviation is computed (e.g., $$\sigma = \sqrt{\frac{P(P-1)}{C}}) \text{ (416)}.$$

Using the standard deviation, a confidence interval can be determined based on the portion of positive reaction chambers and the standard deviation. As an example, $$P_{Low,High} = P \mp 1.96\sqrt{\frac{P(1-P)}{C}}.$$

The estimated concentration (λ) is computed as a function of the portion of positive reaction chambers (e.g., λ=−ln(1−p)) (418). The estimated concentration, which is greater than the portion of positive chambers, provides an estimate of the concentration of molecules per panel for the tested biological sample. A confidence interval is computed for the estimated concentration as a function of the portion of positive reaction chambers and the standard deviation (420). In an embodiment, the confidence interval for the estimated concentration is bounded by:

$$\lambda_{Low} = -\ln(1 - P_{Low}) \text{ and } \lambda_{High} = -\ln(1 - P_{High}),$$

where $$P_{High,Low} = P \pm z_c\sqrt{\frac{P(1-P)}{C}}.$$

It should be appreciated that the specific steps illustrated in FIG. 4 provide a particular method of determining a concentration of DNA molecules in a test panel according to an embodiment of the present invention according to an embodiment of the present invention. Other sequences of steps may also be performed according to alternative embodiments. For example, alternative embodiments of the present invention may perform the steps outlined above in a different order. Moreover, the individual steps illustrated in FIG. 4 may include multiple sub-steps that may be performed in various sequences as appropriate to the individual step. Furthermore, additional steps may be added or removed depending on the particular applications. One of ordinary skill in the art would recognize many variations, modifications, and alternatives.

Figure 5:
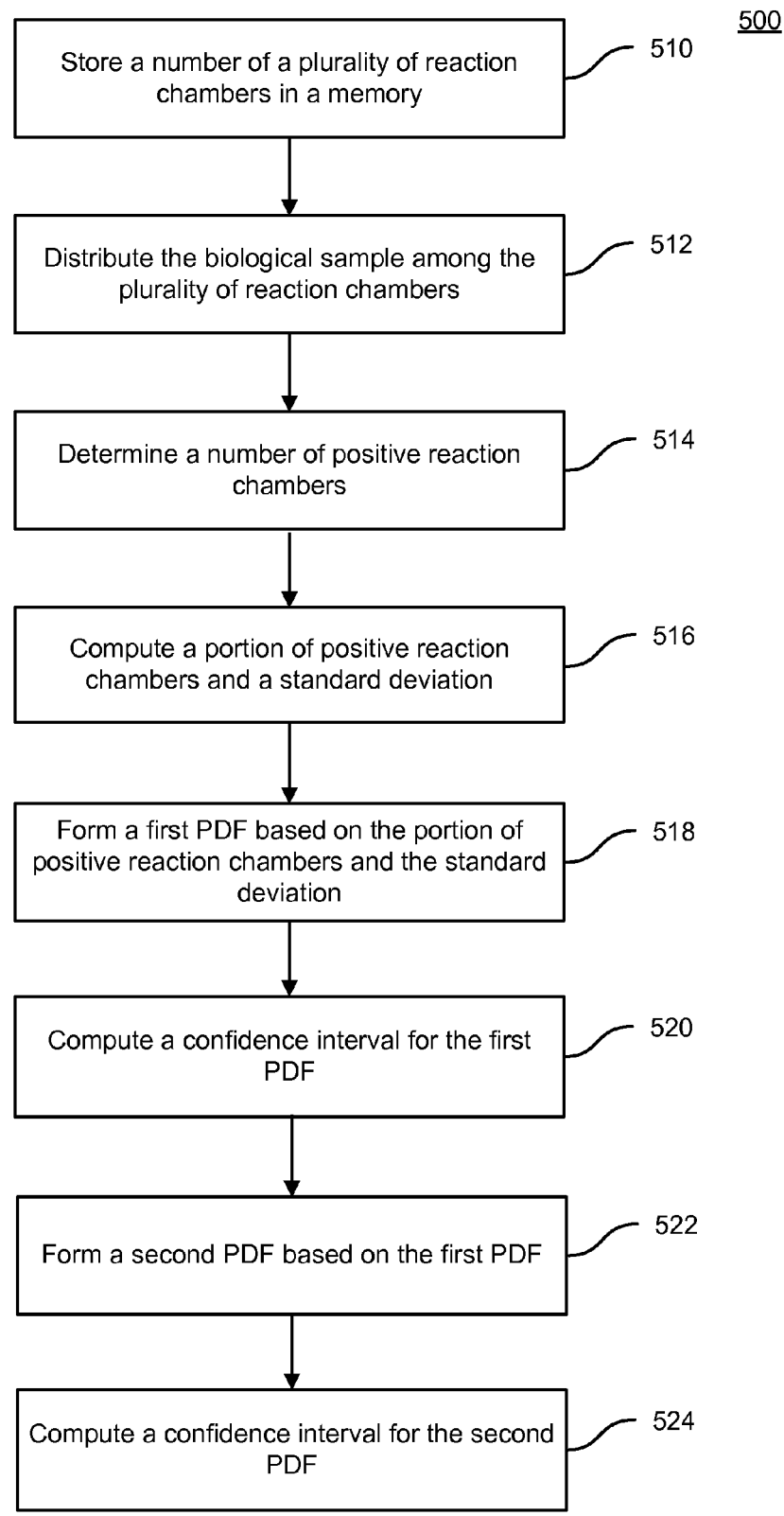
FIG. 5 is a simplified flowchart illustrating a method of determining a concentration of DNA molecules according to another embodiment of the present invention.

FIG. 5 is a simplified flowchart illustrating a method 500 of determining a concentration of DNA molecules according to another embodiment of the present invention. The number of reaction chambers in a panel is stored into a memory (510). In some embodiments, a digital array may include a number of adjacent panels (e.g., 12 panels) as illustrated in FIG. 1. The number of reaction chambers, for example, C=765, can be input using suitable input devices such as a keyboard of a computer system. The memory is provided as part of the sample analysis system. The biological sample is distributed among the reaction chambers (512). In a particular embodiment, the biological sample is partitioned using a digital array to form a number of reaction chambers in which the concentration of DNA molecules is less than one per chamber. After partitioning in the digital array in this particular embodiment, the biological sample is thermocycled and imaged to determine a number of positive reaction chambers (514). In embodiments of the present invention, positive reaction chambers (denoted by the symbol H) are those reaction chambers associated with one or more DNA molecules of interest.

The portion of the reaction chambers in the panel that are positive reaction chambers is computed (e.g., P=H/C) and a standard deviation is computed (e.g., $$\sigma = \sqrt{\frac{P(P-1)}{C}}\ )\ (516).$$

Using the standard deviation, a confidence interval can be determined based on the portion of positive reaction chambers and the standard deviation. As an example, $$P_{Low,High} = P \mp 1.96\sqrt{\frac{P(1-P)}{C}}.$$

A first probability density function (PDF) is formed based on the portion of positive reaction chambers and the standard deviation previously computed (518). As an example, the PDF may be a Gaussian (normal) distribution in which the mean of the PDF is the portion of positive reaction chambers and the standard deviation is $\sigma$. Utilizing the first PDF (which may be referred by the symbol F), a confidence interval for the first PDF is computed based on predetermined confidence interval values (X) by measuring the X % area under the PDF centered on the mean. Thus, a confidence interval for the first PDF is defined by $P_{Low}$ and $P_{High}$ (520).

A second PDF is formed (which may be referred to by the symbol G) representing a distribution of estimated concentrations (522). The second PDF is formed by considering values of estimated concentration $\lambda$ and computing estimated hit probabilities as $p=1-e^{-\lambda}$. Given a computed value p, the second histogram is computed as:

$$G(\lambda)=F(p)(1-p).$$

Utilizing the second PDF (G), a confidence interval for the second PDF is computed based on predetermined confidence interval values (Y) by measuring the Y % area under the second PDF centered on the estimated mean concentration ($\lambda_{mean}$). Thus, a confidence interval for the second PDF is defined by $\lambda_{Low}$ and $\lambda_{High}$ (524). In an embodiment, the output of the method includes the second PDF, the estimated mean concentration, the confidence interval parameters, combinations, thereof, and the like.

It should be appreciated that the specific steps illustrated in FIG. 5 provide a particular method of determining a concentration of DNA molecules in a test panel according to another embodiment of the present invention according to an embodiment of the present invention. Other sequences of steps may also be performed according to alternative embodiments. For example, alternative embodiments of the present invention may perform the steps outlined above in a different order. Moreover, the individual steps illustrated in FIG. 5 may include multiple sub-steps that may be performed in various sequences as appropriate to the individual step. Furthermore, additional steps may be added or removed depending on the particular applications. One of ordinary skill in the art would recognize many variations, modifications, and alternatives.

Figure 9A:
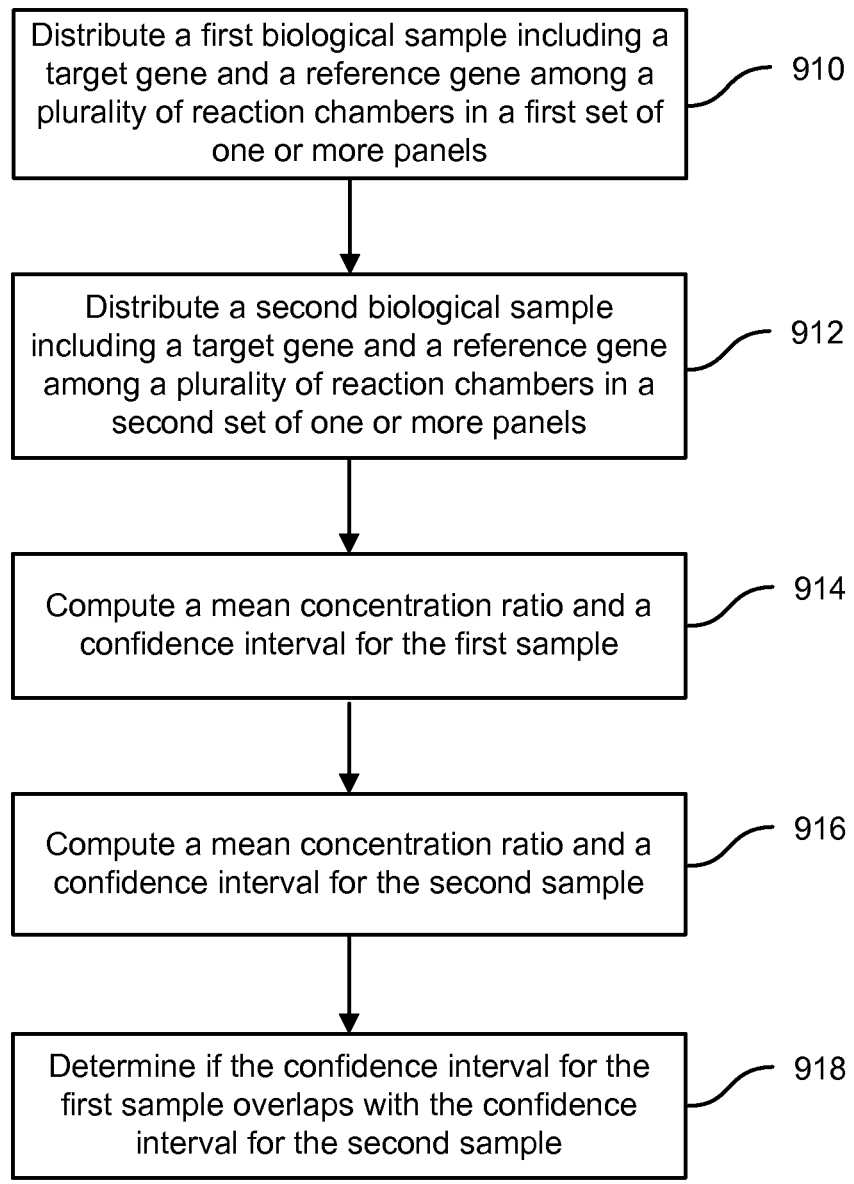
FIG. 9A is a simplified flowchart illustrating a method of determining if two samples have different concentrations of a target gene according to an embodiment of the present invention.

FIG. 9A is a simplified flowchart illustrating a method 900 of determining if two samples have different concentrations of a target gene according to an embodiment of the present invention. A first biological sample is distributed among a plurality of reaction chambers in a first set of one or more panels (910). The first biological sample includes a target gene and a reference gene. A second biological sample is then distributed among a plurality of reaction chambers in a second set or one or more panels (912). Thus, in the embodiment illustrated in FIG. 9A, different biological samples are randomly distributed in two identical or similar sets of one or more panels. The first and second samples may include the same target gene, but with a differing number of copies of the target gene between the samples.

A mean concentration ratio and a confidence interval is computed for the first sample (914). Various techniques as described throughout the present specification can be utilized to estimate the mean concentration ratio between the target and reference genes. For example, the methods described in relation to FIG. 6 and/or FIG. 7. A mean concentration ratio and a confidence interval is computed for the second sample (916). As with the computations for the first sample, various techniques as described throughout the present specification can be utilized to estimate the mean concentration ratio between the target and reference genes for the second sample, for example, the methods described in relation to FIG. 6 and/or FIG. 7. Utilizing the mean concentration ratios and confidence intervals, a determination is made if the confidence interval for the first sample overlaps with the confidence interval for the second sample (918). As described in relation to FIG. 9B, if the confidence intervals do not overlap, then the number of panels used is sufficient to provide estimates of the copy numbers per target gene with sufficient accuracy define by the confidence intervals. If there is overlap between the confidence intervals, then an additional number of panels may be utilized to decrease the confidence intervals and reduce overlap.

It should be appreciated that the specific steps illustrated in FIG. 9A provide a particular method of determining if two samples have different concentrations of a target gene according to another embodiment of the present invention. Other sequences of steps may also be performed according to alternative embodiments. For example, alternative embodiments of the present invention may perform the steps outlined above in a different order. Moreover, the individual steps illustrated in FIG. 9A may include multiple sub-steps that may be performed in various sequences as appropriate to the individual step. Furthermore, additional steps may be added or removed depending on the particular applications. One of ordinary skill in the art would recognize many variations, modifications, and alternatives.

Figure 9B:
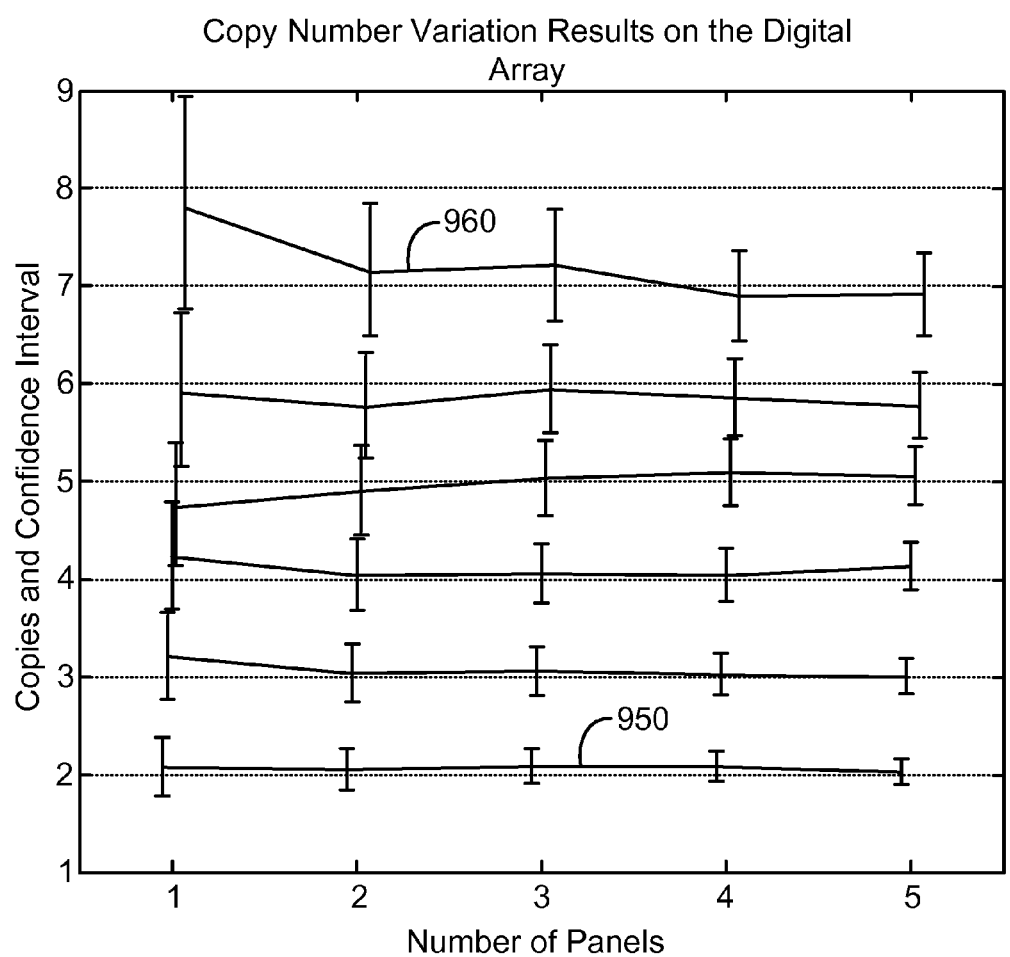
FIG. 9B is a chart showing data from a CNV study to distinguish between samples with varying numbers of copies of a target gene according to an embodiment of the present invention.

FIG. 9B is a chart showing data from a CNV study to distinguish between samples with varying numbers of copies of a target gene according to an embodiment of the present invention. As illustrated in FIG. 9B, the data from an actual CNV study using a digital array provides insight into distinguishing between samples with varying number of copies of a target gene. In total, six different known ratios were estimated by running experiments for a varying number of panels. The graphs for different numbers of copies are slightly staggered to allow visual comparison of overlap of the 95% confidence intervals.

The copy number variation results for known ratios of 1, 1.5, 2, 2.5, 3 and 3.5 are shown in FIG. 9B. Thus, six different samples are illustrated in FIG. 9B, each of the samples having a different number of copies per target gene. The same target gene and the same reference gene may be utilized in the various samples, but with different numbers of copies of the same target gene. For two copies of the target gene, the ratio of the number of copies of the target gene to the reference gene is 1 (curve 950) and for seven copies of the target gene, the ratio is 3.5 (curve 960).

As the number of panels increases, then the number of chambers increases (a multiple of 765 in some digital arrays) and therefore the estimation of the ratio becomes more accurate. Accordingly, the confidence interval shrinks as the number of panels increases. When only a single panel is utilized, there is significant overlap between 95% confidence intervals of certain ratios (e.g. between ratio 2 and 2.5, represented by copy number 4 and 5 on the ordinate axis). Using two panels, some copy numbers are distinguishable (e.g., between ratio 1.5 and 2, represented by copy number 3 and 4), but other differences in terms of the number of copies of the target gene cannot be distinguished as represented by the overlap of the confidence intervals (e.g. between ratio 2.5 and 3, represented by copy number 5 and 6).

When three or more panels are utilized, there is no overlap, regardless of the copy number variation ratio. In all cases using three or more panels, the known ratio lies within the computed 95% confidence interval. Note that using the methods and systems described herein, one can find the optimal numbers of positive chambers for each ratio that will give the smallest confidence intervals and therefore improve the results.

Because the digital array available from the present assignee includes 12 panels per biochip, using a single biochip, it is possible to distinguish copy number variations associated with ratios much higher than illustrated in FIG. 9B. Additionally, as discussed above, as the reaction chamber volume is reduced, additional chambers may be provided in a given unit area, providing additional resolution for the estimation of the ratio. As a result, increased accuracy or a given accuracy from a given number of panels are provided by designs in accordance with the present invention having reduced chamber volumes.

Figure 6:
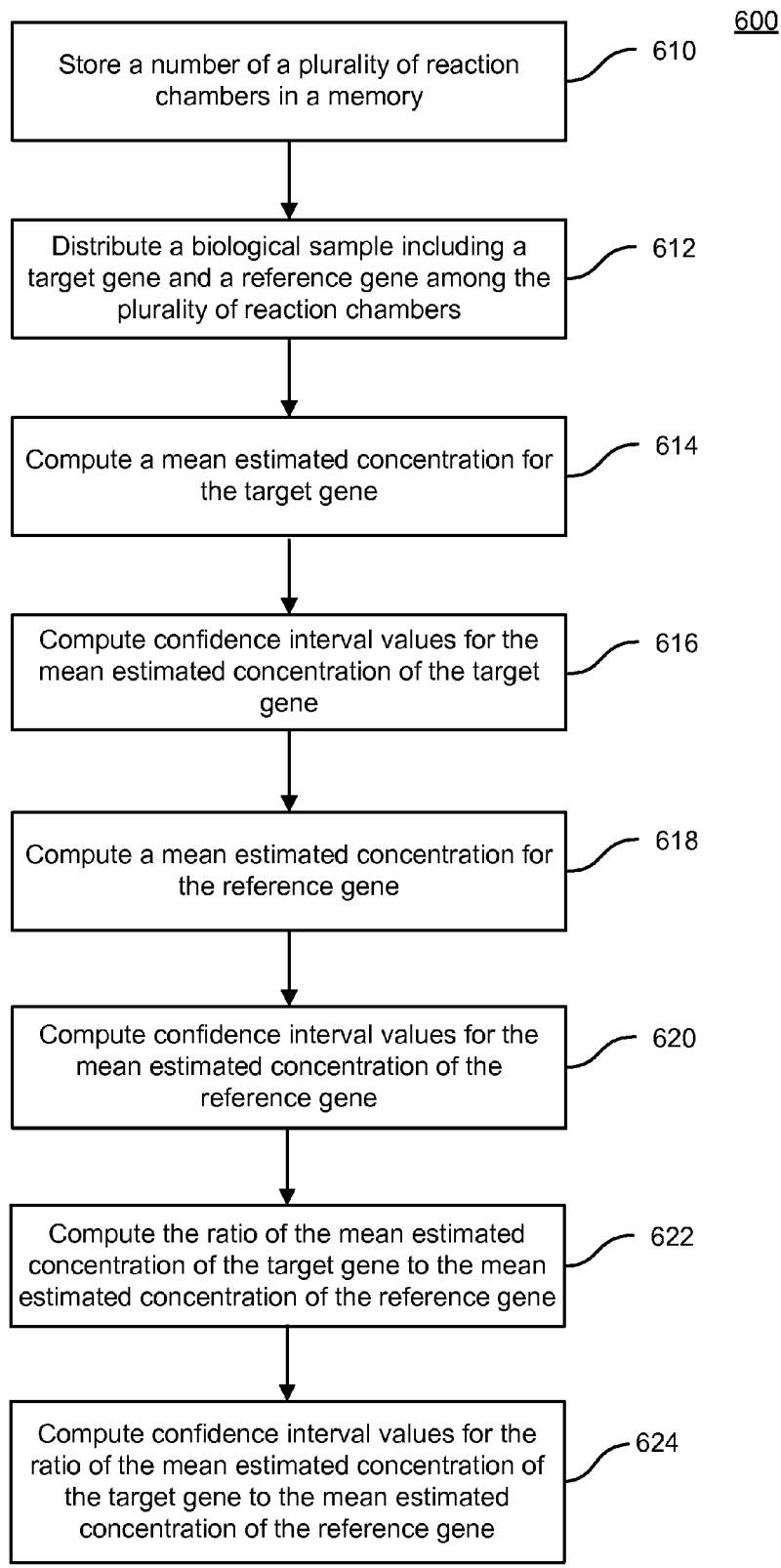
FIG. 6 is a simplified flowchart illustrating a method of determining a ratio of target to reference gene concentration according to an embodiment of the present invention.

FIG. 6 is a simplified flowchart illustrating a method 600 of determining a ratio of target to reference gene concentration according to an embodiment of the present invention. In CNV studies, one goal is to determine the ratio of true concentrations of two genes, one being a reference gene and the other being a test gene, along with the associated confidence interval. A number of reaction chambers are stored in a memory (610). A biological sample is distributed among the various reaction chambers, for example, by using a digital array (612). The biological sample includes both a target gene and a reference gene. The distribution of the biological sample is random, thereby providing for a concentration of less than one gene per reaction chamber. A mean estimated concentration for the target gene is computed (614) and a confidence interval is computed for the mean estimated concentration for the target gene (616). The mean estimated concentration (e.g., $\lambda_{T,mean}$) and the confidence interval values (e.g., $\lambda_{T,Low}$ and $\lambda_{T,High}$) can be computed using the methods described in relation to either FIG. 4 of FIG. 5. Thus, in some embodiments, the values computed for the mean estimated concentration for the target gene will be based on approximate calculations, whereas in other embodiments, they will be based on PDF-based calculations. One of ordinary skill in the art would recognize many variations, modifications, and alternatives.

A mean estimated concentration for the reference gene is computed (618) and a confidence interval is computed for the mean estimated concentration for the reference gene (620). The mean estimated concentration (e.g., $\lambda_{R,mean}$) and the confidence interval values (e.g., $\lambda_{R,Low}$ and $\lambda_{R,High}$) can be computed using the methods described in relation to either FIG. 4 of FIG. 5. A ratio of the mean estimated concentration of the target gene to the mean estimated concentration of the reference gene is computed (622) as $r_{mean} = \lambda_{T,mean}/\lambda_{R,mean}$. Confidence interval values (e.g., $r_{Low}$ and $r_{High}$) for the ratio of the mean estimated concentration of the target gene to the mean estimated concentration of the reference gene are computed (624). In computing the confidence interval values, the following equations are utilized in one embodiment:

$$H_{Top} = \lambda_{T,High} - \lambda_{T,mean} \text{ and } H_{Bottom} = \lambda_{T,mean} - \lambda_{T,Low}$$

$$W_{Right} = \lambda_{R,High} - \lambda_{R,mean} \text{ and } W_{Left} = \lambda_{R,mean} - \lambda_{R,Low}$$

$$r_{Low} = \frac{\lambda_T \lambda_R - \sqrt{\lambda_T^2 \lambda_R^2 - (H_{Bottom}^2 - \lambda_T^2)(W_{Right}^2 - \lambda_R^2)}}{\lambda_R^2 - W_{Right}^2}$$

$$r_{High} = \frac{\lambda_T \lambda_R + \sqrt{\lambda_T^2 \lambda_R^2 - (H_{Top}^2 - \lambda_T^2)(W_{Left}^2 - \lambda_R^2)}}{\lambda_R^2 - W_{Left}^2}$$

It should be appreciated that the specific steps illustrated in FIG. 6 provide a particular method of determining a ratio of target to reference gene concentration according to an embodiment of the present invention. Other sequences of steps may also be performed according to alternative embodiments. For example, alternative embodiments of the present invention may perform the steps outlined above in a different order. Moreover, the individual steps illustrated in FIG. 6 may include multiple sub-steps that may be performed in various sequences as appropriate to the individual step. Furthermore, additional steps may be added or removed depending on the particular applications. One of ordinary skill in the art would recognize many variations, modifications, and alternatives.

Figure 7:
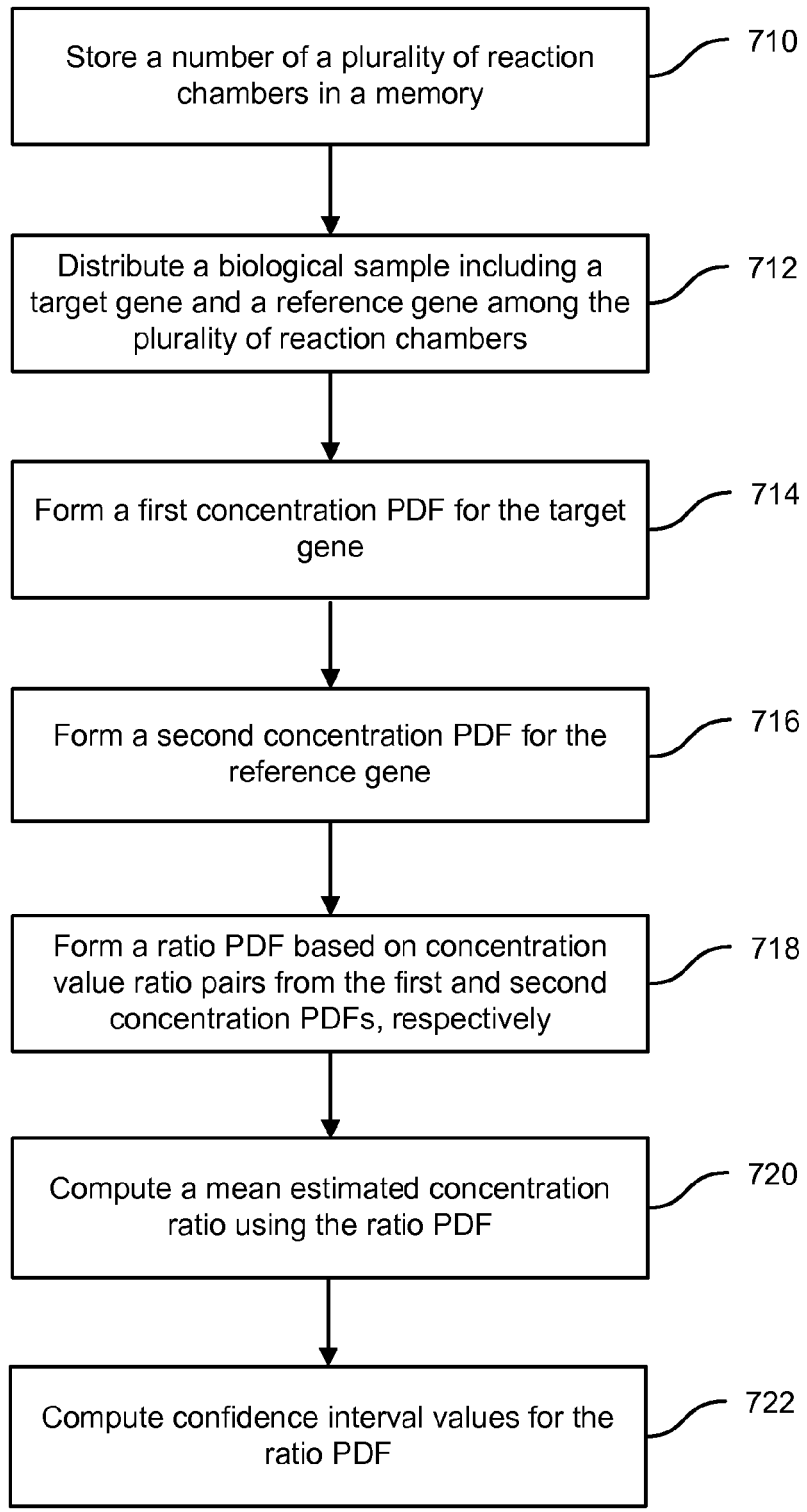
FIG. 7 is a simplified flowchart illustrating a method of determining a ratio of target to reference gene concentration according to another embodiment of the present invention.

FIG. 7 is a simplified flowchart illustrating a method 700 of determining a ratio of target to reference gene concentration according to another embodiment of the present invention. A number of reaction chambers are stored in a memory (710). A biological sample is distributed among the various reaction chambers, for example, by using a digital array (712). The biological sample includes both a target gene and a reference gene. The distribution of the biological sample is random, thereby providing for a concentration of less than one gene per reaction chamber.

A first concentration PDF for the target gene is formed (e.g., $G_1$) and a second concentration PDF for the reference gene is formed (e.g., $G_2$) (714 and 716). In forming the first and second concentration PDFs, the methods described in relation to FIG. 5 are utilized in a particular embodiment. In an exemplary embodiment, formation of the first and second concentration PDFs includes computation of mean estimated concentrations and associated confidence interval values.

A ratio PDF is formed based on concentration value ratio pairs from the first and second concentration PDFs, respectively (718). In order to form the ration PDF (L), the range covered by the ratio PDF is divided into bins. For each bin, possible pairs of $\lambda_T$ and $\lambda_R$ are considered for which the ratio $r = \lambda_T/\lambda_R$ falls within the bin. Typically, all possible pairs for which the ration falls within the bin are considered. For all such pairs, the products of $G_1(\lambda_1)$ and $G_2(\lambda_2)$ are summed to form entries in the L(r) PDF. Utilizing the ratio PDF (L(r)), a confidence interval for the ratio PDF is computed based on predetermined confidence interval values (X) by measuring the X % area under the ratio PDF centered on the estimated mean ratio ($r_{mean}$). Thus, a confidence interval for the ratio PDF is defined by $r_{Low}$ and $r_{High}$ (722). In an embodiment, the output of the method includes the ratio PDF, the estimated mean ratio, the confidence interval parameters, combinations, thereof, and the like.

It should be appreciated that the specific steps illustrated in FIG. 7 provide a particular method of determining a ratio of target to reference gene concentration according to another embodiment of the present invention. Other sequences of steps may also be performed according to alternative embodiments. For example, alternative embodiments of the present invention may perform the steps outlined above in a different order. Moreover, the individual steps illustrated in FIG. 7 may include multiple sub-steps that may be performed in various sequences as appropriate to the individual step. Furthermore, additional steps may be added or removed depending on the particular applications. One of ordinary skill in the art would recognize many variations, modifications, and alternatives.

In forming the ratio PDF, the assumption, which is valid for embodiments of the present invention, is made that $\Lambda_1$ and $\Lambda_2$ are independent. A sampling distribution L of the ratio of random variable $R=\Lambda_1/\Lambda_2$ is computed as follows:

$$\int_{r1}^{r2} L(R) dR = \iint_{r1 \leq R \leq r2} G(\Lambda_1) F(\Lambda_2) d\Lambda_1 d\Lambda_2$$

A graphical interpretation of this formula is cutting out thin wedges in the joint distribution of $G(\Lambda_1)$ and $F(\Lambda_2)$ and accumulating the probabilities inside the wedge to compute the distribution L in the corresponding thin interval of the ratio. This is the basis of the methods and systems that implement integration in order to compute L(R):

1) Build histograms of sampling distributions $G(\Lambda_1)$ and $F(\Lambda_2)$. The tails of the histograms where probabilities become very small are approximated by zero.

2) Build a histogram L(R) of sampling distribution of the ratio random variable $R=\Lambda_1/\Lambda_2$ by considering each bin $[r_1, r_2]$ and by adding all the joint probabilities of different values of concentrations which give a ratio $r \in [r_1, r_2]$.

3) Compute the mean and the 95% confidence interval from the ratio histogram.

It will be noted that one can still use direct formulas, as an approximation, to compute confidence interval as follows: The means of G and F are $\lambda_1$ and $\lambda_2$ respectively. Let the standard deviations be $\sigma_x$ and $\sigma_y$, respectively. Assuming that distributions are normal, it follows that the boundary of the confidence ellipse for a given confidence level $z_c$ would be defined by:

$$\frac{(x-\lambda_2)^2}{\sigma_x^2} + \frac{(y-\lambda_1)^2}{\sigma_y^2} = z_c^2.$$

It is easy to generalize this to embodiments of the present invention, under a reasonably close approximation, when we have asymmetric distributions which are assumed to be normal in each of the four quadrants of the coordinate system centered at $(\lambda_2, \lambda_1)$. Then the confidence region is made of the union of four quadrant-wise elliptic regions. Let the asymmetric confidence interval for specified $z_c$ of $\Lambda_1$ be $[\lambda_1-H_B, \lambda_1+H_T]$ and of $\Lambda_2$ be $[\lambda_2-W_L, \lambda_2+W_R]$.

If $W_R=W_L=z_c\sigma_x$ and $H_T=H_B=z_c\sigma_y$, it is symmetric case. It can be shown that the slopes of lines that will be tangents to this union of four quadrant-wise ellipses will be:

$$r_{Low} = \frac{\lambda_1\lambda_2 - \sqrt{\lambda_1^2\lambda_2^2 - (H_B^2 - \lambda_1^2)(W_R^2 - \lambda_2^2)}}{\lambda_2^2 - W_R^2}$$

$$r_{High} = \frac{\lambda_1\lambda_2 + \sqrt{\lambda_1^2\lambda_2^2 - (H_T^2 - \lambda_1^2)(W_L^2 - \lambda_2^2)}}{\lambda_2^2 - W_L^2}.$$

The above equations can be used as an approximation though a numerical algorithm will give more accurate results as the algorithm does not make any assumptions and works with arbitrary sampling distributions. It should be noted that is some embodiments, special care is taken if the confidence region gets too close to the $\Lambda_1$ axis when $\Lambda_2$ is small. If it touches the $\Lambda_1$ axis, then $r_{High}=\infty$. If either $\lambda_1$ or $\lambda_2$ is too small, one can build the histogram of $\Lambda_2$ or $\Lambda_2$, respectively, with a smaller bin size to get accurate results. This is possible because $\Lambda_1$ and $\Lambda_2$ are random variables that take real values.

As described more fully throughout the specification, the following equations or combinations of the following equations are utilized in various embodiments of the present invention that implement methods and systems to determine copy number variation:

$$P_1 = \frac{H_1}{C}, P_2 = \frac{H_2}{C}$$

$$S_1 = \sqrt{\frac{P_1(1-P_1)}{C}}, S_2 = \sqrt{\frac{P_2(1-P_2)}{C}}$$

$$P_{1,Low} = P_1 - 1.96S_1, P_{1,High} = P_1 + 1.96S_1$$

$$P_{2,Low} = P_2 - 1.96S_2, P_{2,High} = P_2 + 1.96S_2$$

$$\lambda_1 = -\ln(1-P_1), \lambda_{1,Low} = -\ln(1-P_{1,Low}),$$

$$\lambda_{1,High} = -\ln(1-P_{1,High})$$

$$\lambda_2 = -\ln(1-P_2), \lambda_{2,Low} = -\ln(1-P_{2,Low}),$$

$$\lambda_{2,High} = -\ln(1-P_{2,High})$$

$$H_{Top} = \lambda_{1,High} - \lambda_1, H_{Bottom} = \lambda_1 - \lambda_{1,Low}$$

$$W_{Right} = \lambda_{2,High} - \lambda_2, W_{Left} = \lambda_2 - \lambda_{2,Low}$$

$$r = \frac{\lambda_1}{\lambda_2}$$

$$r_{Low} = \frac{\lambda_1\lambda_2 - \sqrt{\lambda_1^2\lambda_2^2 - (H_{Bottom}^2 - \lambda_1^2)(W_{Right}^2 - \lambda_2^2)}}{\lambda_2^2 - W_{Right}^2}$$

$$r_{High} = \frac{\lambda_1\lambda_2 + \sqrt{\lambda_1^2\lambda_2^2 - (H_{Top}^2 - \lambda_1^2)(W_{Left}^2 - \lambda_2^2)}}{\lambda_2^2 - W_{Left}^2}$$

In these equations, the following variables are utilized: a number of reaction chambers C and counts $H_1$ and $H_2$ of the positive chambers in a digital array for the target gene and the reference gene, respectively. Utilizing proper assumptions, these equations give close approximations to actual values.

Although embodiments of the present invention are applied to the use of a digital array, this is not required. Other applications in which sampling errors occur are suitable for application of the methods and systems described herein.

For example, dilution of DNA samples, emulsion PCR, droplet-based digital microfluidics techniques (e.g., Raindance Technologies of Guilford, Conn.), blind filling of chambers followed by emulsion blockage of the chamber entry, and the like. Additionally, although embodiments of the present invention have been applied to the problem of determining copy number variation, other applications in which estimates of molecule concentration are provided may benefit from the techniques described herein. Merely by way of example, absolute quantitative analysis based on segregation is addressed by embodiments of the present invention. One of ordinary skill in the art would recognize many variations, modifications, and alternatives.

The inventors have performed computer simulations using a random number generator and a computer program implementing the methods and systems described herein, choosing a ratio of 2, and building a distribution of estimated ratios over 50 thousand panels. In 94.9% of the panels, the true chosen ratio did lie in the computed confidence intervals thereby showing the correctness of the methods and systems described herein.

Figure 8A:
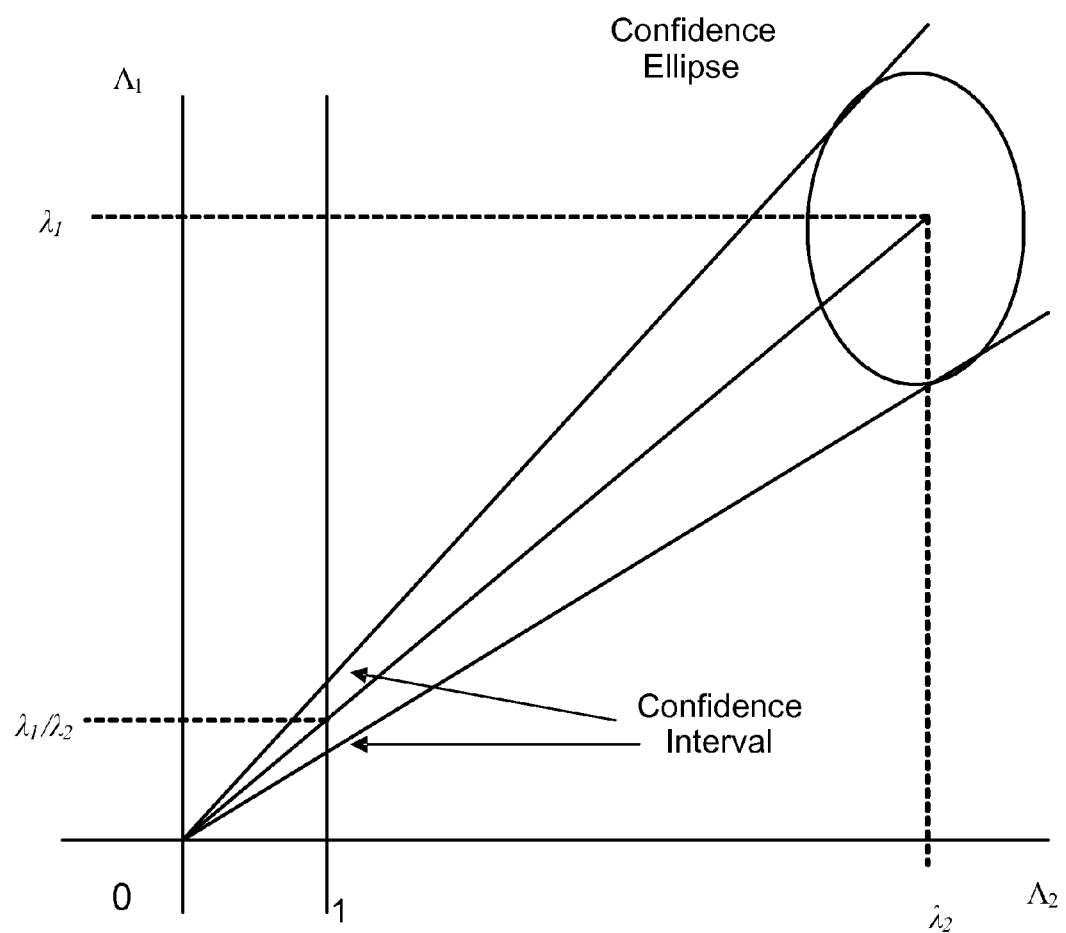
FIG. 8A is a simplified graph illustrating the computation of confidence intervals of a ratio of two normally distributed random variables according to an embodiment of the present invention.
Figure 8B:
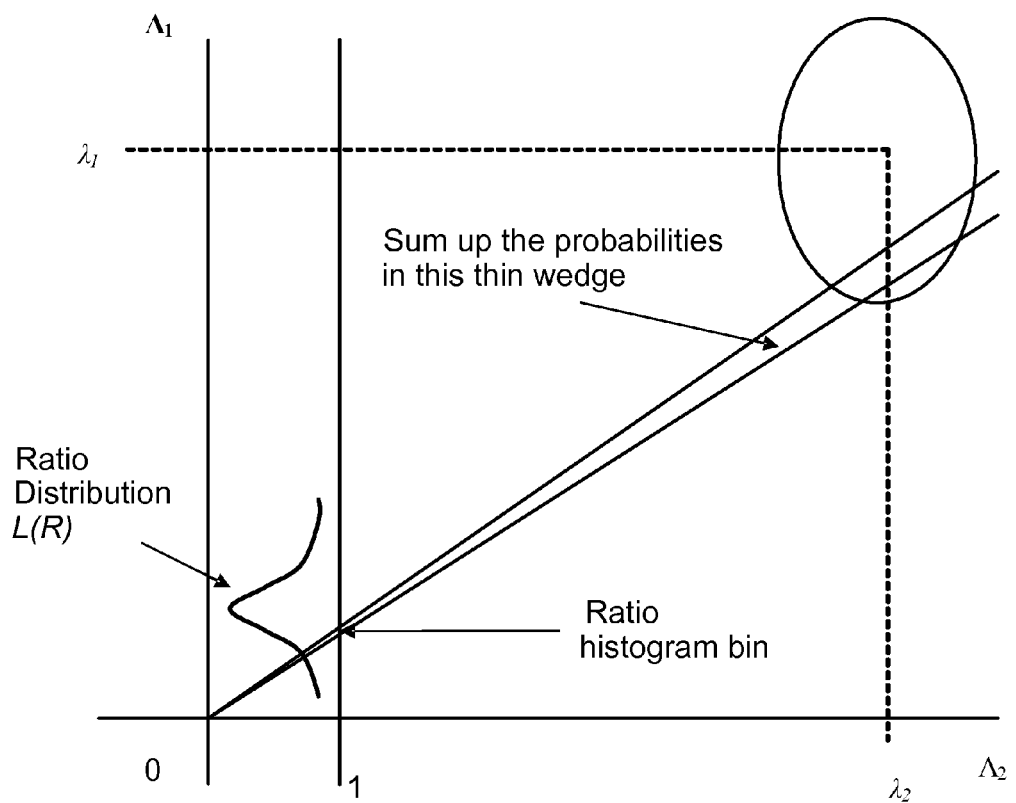
FIG. 8B is a simplified graph illustrating the computation of a sampling distribution of the ratio of two random variables with arbitrary probability distributions according to an embodiment of the present invention.

In discussing the method of forming the ratio PDF, reference is made to FIG. 8A and FIG. 8B. FIG. 8A illustrates a geometric interpretation of Fieller's Theorem to compute a confidence interval of a ratio of two normally distributed random variables $\Lambda_1$ and $\Lambda_2$ in which the confidence ellipse of the joint sampling distribution is projected on a vertical line. FIG. 8B illustrates a numerical projection algorithm used to compute the sampling distribution of the ratio of two random variables with arbitrary probability distributions by slicing the 2-D space into thin wedges and accumulating the joint probabilities in the wedges. Most of the contribution would come from the confidence ellipse region.

In developing the methods and systems described here, the inventors have determined that if one can let the sampling distributions of the test gene and the reference gene be $G(\Lambda_1)$ and $F(\Lambda_2)$, respectively. If these distributions were normal, then one can make use of Fieller's Theorem. However, as mentioned previously, one can not make this assumption in general. Thus, the inventor have developed a geometric interpretation of Fieller's theorem that is applicable to problems with arbitrary sampling distributions.

Assume $G(\Lambda_1)$ and $F(\Lambda_2)$ are normal. For $\lambda_1$ and $\lambda_2$, the ratio $r=\lambda_1/\lambda_2$ can be shown as the slope of the line in the two-dimensional plane which passes through the origin and the 2-D point $(\lambda_2, \lambda_1)$. Consider the two lines which pass through the origin and are tangents to this ellipse. The intersection of these lines with the vertical line at $\Lambda_2=1$ gives the desired confidence interval.

The inventors have made a study of copy number analysis using a Digital Array on the BioMark™ system. A 10-μl reaction mix is normally prepared for each panel. It contains 1× TaqMan Universal master mix (Applied Biosystems, Foster City, Calif.), 1×RNase P-VIC TaqMan assay, 1× TaqMan assay for the target gene (900 nM primers and 200 nM FAM-labeled probe), 1× sample loading reagent (Fluidigm, South San Francisco, Calif.) and DNA with about 1,100-1,300 copies of the RNase P gene. 4.59 μl of the 10-μl reaction mix was uniformly partitioned into the 765 reaction chambers of each panel and the digital array was thermocycled on the BioMark™ system. Thermocycling conditions included a 95° C., 10 minute hot start followed by 40 cycles of two-step PCR: 15 seconds at 95° C. for denaturing and 1 minute at 60° C. for annealing and extension. Molecules of the two genes were independently amplified. FAM and VIC signals of all chambers were recorded at the end of each PCR cycle. After the reaction was completed, Digital PCR Analysis software (Fluidigm, South San Francisco, Calif.) was used to process the data and count the numbers of both FAM-positive chambers (target gene) and VIC-positive chambers (RNase P) in each panel.

A spike-in experiment was performed using a synthetic construct to explore the digital array's feasibility as a robust platform for the CNV study. A 65-base oligonucleotide was ordered from Integrated DNA Technologies (Coralville, Iowa) that is identical to a fragment of the human RPP30 gene. The sequences of the primers and FAM-BHQ probe used to amplify this construct are from Emery. The primers and probe were ordered from Biosearch Technologies (Novato, Calif.).

Both RPP30 synthetic construct and human genomic DNA NA10860 (Coriell Cell Repositories Camden, N.J.) were quantitated using the RPP30 assay on a digital array. Different amounts of RPP30 synthetic construct was then added into the genomic DNA so that mixtures with ratios of RPP30 to RNase P of 1:1 (no spike-in), 1:1.5, 1:2, 1:2.5, 1:3, and 1:3.5 were made simulating DNA samples containing 2 to 7 copies of the RPP30 gene per diploid cell. These DNA mixtures were analyzed on the digital arrays as described above. Five panels were used for each mixture and 400-500 RNase P molecules were present in each panel. The ratios of RPP30/RNase P of all samples were calculated using the techniques developed in this paper. For each ratio, we did pooled analysis by adding the numbers of positive chambers in the first P=1, 2, 3, 4, 5 panels. These results are described in relation to FIG. 9A and FIG. 9B.

Figure 12:
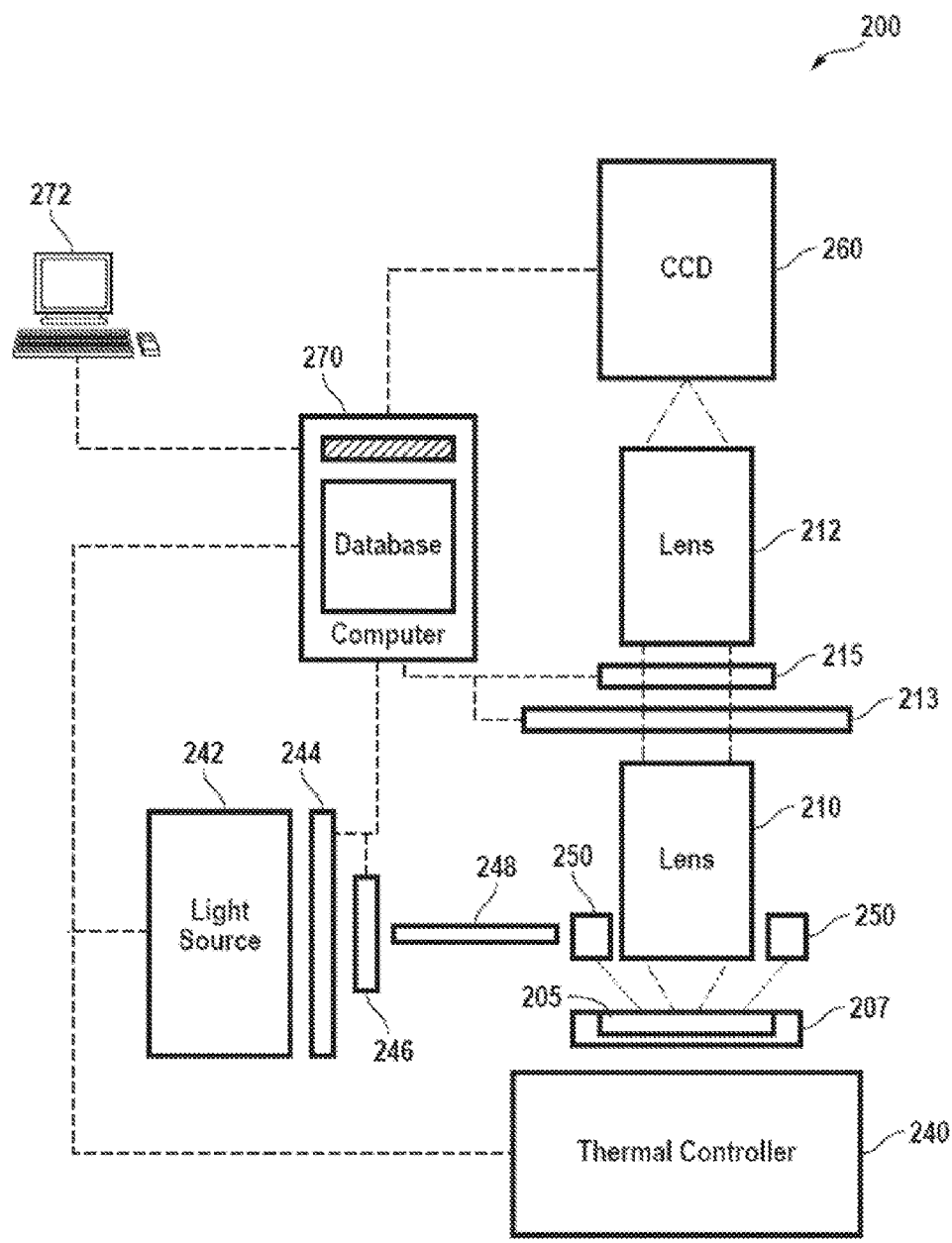
FIG. 12 is a simplified schematic diagram of an analysis system according to an embodiment of the present invention.

FIG. 12 is a simplified schematic diagram of an analysis system according to an embodiment of the present invention. As illustrated in FIG. 12, optical imaging systems provided according to some embodiments of the present invention include fluorescence imaging systems coupled to thermal control modules. Such systems are adapted to collect data from microfluidic or nanofluidic chips with N×M geometries. In some embodiments, N is equal to M. For example, embodiments of the present invention utilize microfluidic devices with 32×32 reaction chambers, 48×48 reaction chambers, 96×96 reaction chambers, and other geometries. In a particular embodiment, 96 samples and 96 reagents are utilized in a microfluidic device with a 96×96 reaction chamber geometry. In another particular embodiment, a digital array with multiple panels, each panel having a predetermined number of reaction chambers is utilized. As will be evident to one of skill in the art, the methods and systems provided according to embodiments of the present invention enable one platform to perform multiple applications.

As illustrated in FIG. 12, an optical source 242 is provided according to embodiments of the present invention. As will be described more fully below, in some embodiments of the present invention, light from optical source 242 is utilized to induce fluorescence in a sample. In other embodiments, chemiluminescence is utilized as a indicator. Depending on the embodiment, system components will be added, removed, or used, as will be evident to one of skill in the art. In various embodiments, optical sources including light emitting diodes (LEDs), lasers, arc lamps, incandescent lamps, and the like are utilized. These sources may be polychromatic or monochromatic. In a particular embodiment, the optical source is characterized by a first spectral bandwidth. In a specific embodiment, the optical source is a white light source producing optical radiation over a spectral range from about 400 nm to about 700 nm. Merely by way of example, a Lambda LS 300W Xenon Arc lamp, available from Sutter Instruments of Novato, Calif. is utilized as an optical source is some embodiments of the present invention. As will be evident to one of skill in the art, other optical sources characterized by larger or smaller spectral bandwidths are capable of being utilized in alternative embodiments.

Excitation filter wheel 244 is illustrated in FIG. 12. In some embodiments, for example, those in which the optical source is polychromatic, the excitation filter wheel 244 is utilized to spectrally filter the light emitted by the optical source 242. Of course, multiple filters could also be used. As an example, in an embodiment, the excitation filter wheel provides a number of spectral filters each adapted to pass a predetermined wavelength range as appropriate for exciting specific fluorescence from a sample. As illustrated in FIG. 12, the excitation filter wheel 244 is coupled to computer 270, providing for computer control of the filters. In a particular embodiment, the excitation filter wheel provides a number of spectral filters:

Filter 1: A filter with a center wavelength of 485 nm and a spectral bandwidth of 20 nm;

Filter 2: A filter with a center wavelength of 530 nm and a spectral bandwidth of 20 nm; and Filter 3: A filter with a center wavelength of 580 nm and a spectral bandwidth of 20 nm.

As will be evident to one of skill in the art, embodiments of the present invention are not limited to these particular spectral filters, but will utilize spectral filters adapted for fluorescence processes for particular samples. Moreover, although the previous discussion related to the use of a filter wheel, this is not required by the present invention. In alternative embodiments, spectral filters are provided in geometries other than a wheel. For example, spectral filters that drop into a filter holder, electro-optic filters, filters placed into the optical path by actuators, and the like are included according to embodiments of the present invention. Moreover, in other embodiments, the optical source is a tunable laser adapted to emit radiation at predetermined wavelengths suitable for excitation of fluorescence. One of ordinary skill in the art would recognize many variations, modifications, and alternatives.

As illustrated in FIG. 12, excitation shutter 246 is provided according to embodiments of the present invention. The excitation shutter is operated under control of a computer 270 in some embodiments, to block/pass the optical signal generated by the optical source 242 and spectrally filtered by the excitation filter wheel 244. Depending on the application, the excitation source is blocked while samples are inserted and removed from the system as well as for calibration operations. In some embodiments, the excitation shutter is not utilized, for example, in embodiments utilizing laser sources, which provide alternative means to extinguish the optical source.

When the excitation shutter is operated in an open position, the optical excitation signal passes through a fiber bundle 248 and is directed so as to impinge on a microfluidic device 205 provided in chip carrier 207. The microfluidic device may be a digital array with nanoliter volume reaction chambers. Other embodiments of the present invention utilize quartz light guides, liquid light guides, other scrambling systems, and the like to increase illumination homogeneity. As illustrated in FIG. 12, the excitation optical signal is directed, through reflection by optical illuminator 250, refraction, or combinations thereof, to impinge on a surface of the microfluidic device 205. As illustrated in FIG. 12, illumination of the microfluidic device is via optical illuminator 250. In other embodiments illumination may be coupled to the microfluidic device obliquely from one or more sides of device, via a ring light, or via a portion of the collection optical train (the optical path between the microfluidic device and the detector 260.

In some embodiments, the illumination of the microfluidic device with light produced by the excitation source is provided over a two-dimensional area of the sample. In these embodiments, a large field of view is provided, which enables the performance of fluorescence applications that involve imaging of time resolved chemical processes and reactions. As an example, fluorescent imaging of protein calorimetry and nucleic acid amplification processes are time resolved processes that benefit from embodiments of the present invention. In some of these processes, simultaneously excitation of the fluorescent samples provided in a number of reaction chambers and simultaneous collection of the fluorescent signals produced by the reactions occurring in the number of reaction chambers is desirable. In other processes, for instance, fluorescence lifetime imaging, a brief excitation pulse is followed by detection (and analysis) of the fluorescent signal as it decays in time from an initial level. One of ordinary skill in the art would recognize many variations, modifications, and alternatives.

As an example, nucleic acid amplification processes typically include the target DNA, a thermostable DNA polymerase, two oligonucleotide primers, deoxynucleotide triphosphates (dNTPs), a reaction buffer, and magnesium. Once assembled, the reaction is placed in a thermal cycler, an instrument that subjects the reaction to a series of different temperatures for varying amounts of time. This series of temperature and time adjustments is referred to as one cycle of amplification. Each cycle theoretically doubles the amount of targeted sequence (amplicon) in the reaction. Ten cycles theoretically multiply the amplicon by a factor of about one thousand; 20 cycles, by a factor of more than a million in a matter of hours. In some applications, it is desirable to acquire fluorescent imaging data from a large area (e.g., on the order of several $cm^2$) in a time period ranging from seconds to minutes.

In some embodiments of the present invention, the methods and systems provided by embodiments of the present invention facilitate image capture processes that are performed in a predetermined time period. Merely by way of example, in an embodiment of the present invention a method of imaging microfluidic devices is provided. The method includes capturing an image of a spatial region associated with at least a determined number of chambers of a microfluidic device using an image detection spatial region during a time frame of less than one minute, whereupon the capturing of the image of the spatial region is substantially free from a stitching and/or scanning process.

Embodiments of the present invention provide a variety of time frames for image capture, ranging from 1 millisecond to 1 minute. In some embodiments, time frames for image capture are greater than one minute. Depending on the emission properties associated with the processes performed in the chambers of the microfluidic device, the time frame for image capture will vary. For example, in an embodiment, the time frame is 10 ms, 50 ms, 100 ms, 250 ms, 500 ms, 750 ms, or 1 second. In other embodiments, the time frame is 2 seconds, 5 seconds, 10 seconds, 15 seconds, 20 seconds, 30 seconds, 40 seconds, 50 seconds, or 1 minute. Of course, the time frame will depend on the particular applications.

In some embodiments, the image capture process is performed in a synchronous manner, capturing an image of a determined number of chambers simultaneously. As an example, in an exemplary PCR process, the microfluidic device is maintained at a temperature of 90° C. for a time period of 15 seconds. Subsequently, the microfluidic device is maintained at a temperature of 60° C. for 45 seconds. The heating and cooling cycle is repeated at a one minute cycle period for a number of cycles. Utilizing embodiments of the present invention, images of a determined number of chambers present in the microfluidic device are acquired synchronously, while the chambers are maintained at a uniform temperate as a function of position. For example, a two-dimensional image of an entire microfluidic device may be acquired utilizing a 30 second exposure while the microfluidic device is maintained at the temperature of 60° C. One of skill in the art will appreciate the benefits provided by the present invention over raster scanning or stitching systems, in which images of chambers in a first portion (e.g., an upper left quadrant) of the microfluidic device are acquired prior to images of chambers in a second portion (e.g., a lower right quadrant) of the microfluidic device.

In other embodiments, multiple images are acquired of the determined number of chambers during a time frame of less than one minute. As an example of these embodiments, multiple images associated with multiple fluorophores are acquired in a particular embodiment. During the 45 second time period during which the microfluidic device is maintained at the temperature of 60° C., three consecutive images utilizing exposures of 15 seconds may be acquired for three different fluorophores, for example, Rox™, Vic®, and Fam™. Utilizing these multiple images, differential fluorescence ratios can be calculated and analyzed. Of course, depending on the strength of the fluorescent emissions, the exposure times for the various fluorophores may be modified as appropriate the particular application. In this way, embodiments of the present invention provide for imaging of a microfluidic device in multiple spectral bands while the microfluidic device is maintained a constant temperature. The constant temperature, as illustrated by the previous example, may be a portion of a PCR process including cyclical temperature processes.

Embodiments of the present invention provide methods and systems are also adapted to perform and analyze chemiluminescence processes. In some of these processes, reactions occur on a first time scale and an image of the chemiluminescence process is acquired on a second time scale. In a particular process, the second time scale is less than the first time scale. Thus, embodiments of the present invention are adapted to capture synchronous images of chemiluminescence processes when the samples in the reaction chambers of interest have been reacting for an equal amount of time. In some of these processes, temperature control, including temperature cycling of the samples is provided, whereas in other embodiments, the reaction chambers are maintained at a constant temperature.

As illustrated in FIG. 12, a thermal controller, also referred to as a temperature controller, 240 is provided according to embodiments of the present invention. A number of different options of varying sophistication are available for controlling temperature within selected regions of the microfluidic device or the entire device. Thus, as used herein, the term temperature controller is meant broadly to refer to a device or element that can regulate temperature of the entire microfluidic device or within a portion of the microfluidic device (e.g., within a particular temperature region or at one or more junctions in a matrix of channels of a microfluidic device).

In some embodiments, the microfluidic device is contacted with a thermal control device such that the thermal control device is in thermal communication with the thermal control source so that a temperature of the reaction in at least one of the reaction chamber is changed as a result of a change in temperature of the thermal control source. In different embodiments, the thermal transfer device may comprise a semiconductor, such as silicon, may comprise a reflective material, and/or may comprise a metal.

The thermal control device may be adapted to apply a force to the thermal transfer device to urge the thermal transfer device towards the thermal control source. The force may comprise a mechanical pressure, a magnetic force, an electrostatic force, or a vacuum force in different embodiments. For example, in one embodiment, the force comprises a vacuum force applied towards the thermal transfer device through channels formed in a surface of the thermal control device or the thermal transfer device. A level of vacuum achieved between the surface of the thermal control device and a surface (or a portion of a surface) of the thermal transfer device may be detected. Such detection may be performed with a vacuum level detector located at a position along the channel or channels distal from a location of a source of vacuum. When the vacuum does not exceed a preset level, an alert may be manifested or a realignment protocol may be engaged.

The array device may be contacted with the thermal control device by employment of one or more mechanical or electromechanical positioning devices. Carrying out of the method may be automatically controlled and monitored. For example, such automatic control and monitoring may be performed with an automatic control system in operable communication with a robotic control system for introducing and removing the array device from the thermal control device. The progress of the reactions may also be monitored.

A unit may be provided comprising the thermal control device. A system may be provided comprising the array device and the thermal control device. To ensure the accuracy of thermal cycling steps, in certain devices it is useful to incorporate sensors detecting temperature at various regions of the device. One structure for detecting temperature is a thermocouple. Such a thermocouple could be created as thin film wires patterned on the underlying substrate material, or as wires incorporated directly into the microfabricated elastomer material itself.

Temperature can also be sensed through a change in electrical resistance. For example, change in resistance of a thermistor fabricated on an underlying semiconductor substrate utilizing conventional techniques can be calibrated to a given temperature change. Alternatively, a thermistor could be inserted directly into the microfabricated elastomer material. Still another approach to detection of temperature by resistance is described in Wu et al. in "MEMS Flow Sensors for Nano-fluidic Applications", Sensors and Actuators A 89 152-158 (2001), which is hereby incorporated by reference in its entirety. This paper describes the use of doped polysilicon structures to both control and sense temperature. For polysilicon and other semiconductor materials, the temperature coefficient of resistance can be precisely controlled by the identity and amount of dopant, thereby optimizing performance of the sensor for a given application.

Thermo-chromatic materials are another type of structure available to detect temperature on regions of an amplification device. Specifically, certain materials dramatically and reproducibly change color as they pass through different temperatures. Such a material could be added to the solution as they pass through different temperatures. Thermo-chromatic materials could be formed on the underlying substrate or incorporated within the elastomer material. Alternatively, thermo-chromatic materials could be added to the sample solution in the form of particles.

Another approach to detecting temperature is through the use of an infrared camera. An infrared camera in conjunction with a microscope could be utilized to determine the temperature profile of the entire amplification structure. Permeability of the elastomer material to radiation of appropriate wavelengths (e.g. thermal, infrared, and the like) would facilitate this analysis.

Yet another approach to temperature detection is through the use of pyroelectric sensors. Specifically, some crystalline materials, particularly those materials also exhibiting piezoelectric behavior, exhibit the pyroelectric effect. This effect describes the phenomena by which the polarization of the material's crystal lattice, and hence the voltage across the material, is highly dependent upon temperature. Such materials could be incorporated onto the substrate or elastomer and utilized to detect temperature. Other electrical phenomena, such as capacitance and inductance, can be exploited to detect temperature in accordance with embodiments of the present invention. One of ordinary skill in the art would recognize many variations, modifications, and alternatives.

Imaging system 200 operates, in one embodiment, in the following manner. First, microfluidic device 205 is securely placed on carrier 207. Based on a fixed feature of the microfluidic device 205, for example, an edge of the base support of microfluidic device, computer 270 then causes and x,y drive (not shown) to move the carrier 207 to align the microfluidic device in a first x,y position. In some embodiments, one or more fiducial markings are utilized during the alignment and positioning process. In a specific embodiment, a user of the system then registers the precise coordinate of one or more fiducial marks with the imaging system. In other embodiments, this process is performed automatically as the centroids of the fiducials can be calculated precisely by locating a symmetric XY fiducial object and removing any non-symmetric components. In some embodiments, features of the fiducials, such as edges and corners are utilized during alignment processes. One of ordinary skill in the art would recognize many variations, modifications, and alternatives.

Under the control of computer 270, either adjustments of the carrier 207 to position it in the focal plane of the optical elements 210 and 212 or adjustments of the optical elements 210 and 212 to position the focal plane of the optical elements 210 and 212 to the carrier 207 are performed. In preferred embodiments, the field of view can embrace an entire microfluidic device, including the number of reaction chambers present on the microfluidic device.

The computer 270 includes a processor (cross-hatched element) as well as a database (memory or computer readable media). The computer may be used to implement the methods described herein, including the estimation of DNA concentrations in a sample and the computation of confidence intervals associated with the estimate. Additionally, the computer may be used to determine a ratio of estimated concentrations for one or more genes (e.g., test and reference) along with associated confidence intervals.

A fluorescent, chemiluminescent, or optical signal emitted by the chemical processes occurring in the reaction chambers of the microfluidic device is collected by a first lens system 210. In some embodiments of the present invention, the first lens system is a multi-element optical train including one or more lenses and one or more apertures. As illustrated in FIG. 2A, first lens system 210 includes single lens elements as well as doublets, and the like. The optical properties of the first lens system 210 including focal length, f/#, and the like are selected to provide desired optical performance. One of ordinary skill in the art would recognize many variations, modifications, and alternatives. An emission shutter 215 is illustrated in FIG. 12 to provide for blocking of light rays propagating more than a predetermined distance from the optical axis, although this is not required by the present invention.

Referring once again to FIG. 12, an optical filter device 213 is provided as part of the optical assembly. In some embodiments, the optical filter device is a filter wheel 213 comprising a number of optical elements adapted for passing and optically processing fluorescent or chemiluminescent emissions produced by fluorescently or chemiluminescently labeled reagents. As an example, in an embodiment, a first section of the emission filter wheel is adapted to pass fluorescent emissions produced by a first fluorescent dye, for example, Cy™3 Fluor, available from Amersham Biosciences, part of GE Healthcare of Piscataway, N.J. A second section of the emission filter wheel is adapted to pass fluorescent emissions produced by a second fluorescent dye, for example, Cy™5 Fluor also available from Amersham Biosciences. Of course, the use of these fluorescent dyes is not required by the present invention. In alternative embodiments, Alexa Fluors, available from Invitrogen Corporation of Carlsbad, Calif., are utilized. As an example, in another embodiment, a first section of the emission filter wheel is adapted to pass fluorescent emissions produced by a third fluorescent dye, for example, Alexa Fluor 350, available from Invitrogen Corporation. A second section of the emission filter wheel is adapted to pass fluorescent emissions produced by a fourth fluorescent dye, for example, Alexa Fluor 488, also available from Invitrogen Corporation. Additional details related to the emission filter wheel will be provided below.

In some embodiments, the optical filter device 213 and the emission shutter 215 are located between the first lens system and the second lens system. In some of these embodiments, light rays passing through the optical filter device propagate at small angles with respect to the optic axis. As will be evident to one of skill in the art, spectral filters (e.g., interference filters) placed in regions with small incident ray angle are simpler to design and can potentially provide narrower total spectral bandwidth, through such narrow spectral bandwidth characteristics and/or filter positioning are required by the present invention. As illustrated in FIG. 12, both the optical filter device and the emission shutter are coupled to computer 270, providing for computer control of these elements. Moreover as will be evident to one of skill in the art, multiple, and possibly multiple identical filters, may be provided in the optical path to increase the blockage of excitation wavelengths. In some embodiments these filters are angled with respect to the optic axis so that light rays reflected off of the filters walk out of the optical path.

In other embodiments, certain intercalation dyes that have dramatic fluorescent enhancement upon binding to double-stranded DNA, and/or show strong chemical affinity for double-stranded DNA, can be used to detect double-stranded amplified DNA. Examples of suitable dyes include, but are not limited to, SYBR™ and Pico Green (from Molecular Probes, Inc. of Eugene, Oreg.), ethidium bromide, propidium iodide, chromomycin, acridine orange, Hoechst 33258, Toto-1, Yoyo-1, and DAPI (4',6-diamidino-2-phenylindole hydrochloride). Additional discussion regarding the use of intercalation dyes is provided by Zhu et al., *Anal. Chem.* 66:1941-1948 (1994), which is incorporated by reference in its entirety.

An second lens system 212 is also illustrated in FIG. 12. Fluorescent or chemiluminescent emission passing through the optical filter device 213 and the emission shutter 215 is focused by the second lens system onto a detector 260. In an embodiment, the detector is a CCD camera array, but this is not required by the present invention. In a particular embodiment, an array detector, approximately the size of the microfluidic device, is utilized. Preferably, the pixel size of the detector array 260 is selected to provide an area smaller than the area of the reaction chambers in the microfluidic device, thereby providing multiple detector pixels per reaction chamber. In a particular embodiment, the detector 260 is a CCD array with approximately 15 μm×15 μm pixels.

A number of different detection strategies can be utilized with the microfluidic devices that are provided herein. Selection of the appropriate system is informed in part on the type of event and/or agent being detected. The detectors can be designed to detect a number of different signal types including, but not limited to, signals from radioisotopes, fluorophores, chromophores, electron dense particles, magnetic particles, spin labels, molecules that emit chemiluminescence, electrochemically active molecules, enzymes, cofactors, enzymes linked to nucleic acid probes and enzyme substrates.

Illustrative detection methodologies suitable for use with the present microfluidic devices include, but are not limited to, light scattering, multichannel fluorescence detection, UV and visible wavelength absorption, luminescence, differential reflectivity, and confocal laser scanning. Additional detection methods that can be used in certain application include scintillation proximity assay techniques, radiochemical detection, fluorescence polarization anisotropy, fluorescence lifetime, fluorescence correlation spectroscopy (FCS), time-resolved energy transfer (TRET), fluorescence resonance energy transfer (FRET) and variations such as bioluminescence resonance energy transfer (BRET). Additional detection options include electrical resistance, resistivity, impedance, and voltage sensing.

In some embodiments, detection occurs at a "detection section," or "detection region." These terms and other related terms refer to the portion of the microfluidic device at which detection occurs. In some microfluidic devices, the detection section is generally the reaction chambers present in the microfluidic device. The detection section for matrix-based devices is usually within regions of flow channels that are adjacent an intersection, the intersection itself, or a region that encompasses the intersection and a surrounding region.

The detection section can be in communication with one or more microscopes, diodes, light stimulating devices (e.g., lasers), photomultiplier tubes, processors and combinations of the foregoing, which cooperate to detect a signal associated with a particular event and/or agent. Often the signal being detected is an optical signal that is detected in the detection section by one or more optical detectors. The optical detector can include one or more photodiodes (e.g., avalanche photodiodes), a fiber-optic light guide leading, for example, to a photomultiplier tube or tubes, a microscope, and/or a video camera (e.g., a CCD camera).

Detectors can be microfabricated within the microfluidic device, or can be a separate element. If the detector exists as a separate element and the microfluidic device includes a plurality of detection sections, detection can occur within a single detection section at any given moment. As a specific illustrative example, the microfluidic device can be attached to a translatable stage and scanned under a microscope objective. A signal so acquired is then routed to a processor for signal interpretation and processing. Arrays of photomultiplier tubes can also be utilized. Additionally, optical systems that have the capability of collecting signals from all the different detection sections simultaneously while determining the signal from each section can be utilized.

External detectors are usable because the devices that are provided are completely or largely manufactured of materials that are optically transparent at the wavelength being monitored. This feature enables the devices described herein to utilize a number of optical detection systems that are not possible with conventional silicon-based microfluidic devices.

A particular embodiment of the present invention utilizes a detector in the form of a CCD camera and an optical path that provides for a large field of view and a high numerical aperture to maximize the amount of light collected from each reaction chamber, thereby increasing detection sensitivity. In this embodiment, the CCD is used as an array of photodetectors wherein each pixel or group of pixels corresponds to a reaction chamber rather than being used to produce an image of the array. Thus, the optics may be designed or altered such that image quality is reduced or the image is blurred at the detector in order to increase the useable depth of field of the optical system to collect more light from each reaction chamber. Particularly because the assays contemplated in some embodiments of the present invention include biological assays using fluorescent dyes, which dyes photobleach due to exposure to excitation light hence limiting the total number of signal photons obtainable from a given sample, efficient collection of the limited signal photons can be of importance in instruments such as that discussed. Etendue considerations relate the object and image NA (numerical aperture) and total system magnification for any optical system; since image-side NA can be limited (e.g. by reflection losses at the CCD surface for high-incident-angle rays), in general, arbitrarily high object (sample)-side NA is not achievable simultaneously with arbitrary system magnification. In fact, a larger system magnification can allow a higher object-side NA without requiring a simultaneous (and potentially deleterious for reasons described above) rise in image-side NA. Consequently, in the system described, a large CCD (e.g., 30.7 mm×30.7 mm) focal-plane array has been used to allow for a 1:1 optical system (i.e., a system magnification of 1). This allows a collection NA of 0.36 simultaneous with an image-side NA of 0.36 onto the CCD, which provides reasonable performance with respect to surface reflection losses.

In some embodiments, larger object-side NAs result in reduced object-side depth-of-focus, and hence larger blurring at the detector (assuming blur due to depth of focus greater than or equal to blur due to lens aberrations and other issues) for a given depth of reaction chamber in the sample, limiting the allowable minimum spacing between reaction chambers at the sample if low crosstalk in signal between chambers is to be achieved. In conjunction with a 1:1 optical system, this object-side NA consideration is in good keeping with the ~0.5 NA maximum generally desirable NA onto a CCD (or silicon detector) if one is to avoid reflection losses at the surface thereof. The 1:1 imaging lens system is furthermore inherently free of most odd-order aberrations, increasing the advantage of this particular magnification (M=1). The use of a 1:1 optical system with a detector as large or larger than the microfluidic system to be imaged is thus provided by some embodiments of the present invention as a design for the detailed system.

In other embodiments, there may be a cost constraint related to the size of the detector (e.g. a CCD focal-plane array). For example, some current high quantum-efficiency, full-frame CCD arrays have dimensions of 27.6 mm×27.6 mm. This detector is slightly smaller than a microfluidic device with dimensions of 30.7 mm×30.7 mm, resulting in a system magnification of 0.88 as a design for the system described. Being near system magnification M=1, constraints related to the detector (image-side) incident NA described above are satisfied for such a magnification.

In other embodiments, a given XY-plane (perpendicular to the optical axis) spacing and size of the reaction chambers may be specified (e.g. to achieve a desired density of sample-chambers in the XY-plane), while constraints on the minimum total volume of the chambers remain (e.g. to achieve minimum required chemical volumes, for instance to avoid over-large statistical fluctuations due to small numbers of reagent or target molecules, or simply to achieve a required minimum number of fluorescent or otherwise optically-emitting molecules or objects). In such a case, it may be necessary to extend the chambers parallel to the Z (optical)-axis such that the total volume of each chamber remains equal to or greater than some minimum figure. Greater extension along Z (creating high-aspect ratio, or columnar chambers which concentrate the sample to be interrogated along the Z-axis) will generally result in a larger blur of the chamber image at the detector for given object-side NA, due to depth-of-focus considerations, assuming blur due to depth of focus is greater than or equal to blur due to lens aberrations and other issues. In some situations, this will lead to the user of a lower object-side NA. Use of a lower NA lens system allows for greater depth of focus and hence light collection from a chambers extended parallel to the optic axis without generally incurring inordinate crosstalk in the optical signal between adjacent or nearby chambers. In this way, a greater density of chambers in the X-Y plane (the place perpendicular to the optic axis) may be used without inordinate crosstalk, while the total chamber volume may be kept large by extension of the chambers in Z (parallel to the optic axis). In this case, or other cases where a lower object-side NA is acceptable (e.g., cases where a larger XY spacing of reaction chambers allows for more chamber-image blur at the detector without undue crosstalk; in non-light-limited applications, where higher NA is not essential; where there is sufficient sample that photobleaching is not an issue; non-photobleaching samples, circumstances such as lower acceptable system sensitivity), a lower system magnification (M<1) may be suitable, particularly if $M \geq NA_o/0.5$, or more preferably $M \geq NA_o/0.36$, where $NA_o$=object side NA, or more generally $M \geq NA_o/NA_{det}$ where $NA_{det}$=maximum NA allowable onto the detector face without overlarge reflection/insertion losses to the detector ($NA_{det}$=0.36 to 0.5 for a typical CCD).

In cases where object-side depth-of-focus and/or blur requirements do not necessitate an object-side $NA \leq 0.36$, or possibly 0.5, or more generally $NA_o \leq NA_{det}$, a larger detector is desirable since due to Etendue considerations (as discussed above), since a larger M (generally requiring a larger detector for a given sample size) will allow a smaller $NA_i$ (image-side NA) for a given $NA_o$. Hence where light-collection requirements (e.g. to achieve a certain assay sensitivity) call for a large $NA_o$ (defined by $NA_o > NA_{det}$) and depth-of-focus and other design considerations (e.g. cost) allow for a large $NA_o$, a larger M is desirable such that losses are minimized at the detector. In such embodiments it can be useful to use a detector device, for example, one or more CCD devices, having a size of, or larger than, the area of the microfluidic device to be imaged. Use of such a large detector allows an increase in the magnification of the optical system, and hence (via etendue considerations) higher NA light collection from the sample for a fixed incident NA onto the detector (the latter set, e.g., by reflection losses at the CCD surface at high incoming ray incident angles).

A particularly preferred detector uses a CCD camera and an optical path that provides for a large field of view and a high numerical aperture to maximize the amount of light collected from each reaction chamber, thereby increasing detection sensitivity. In this regard, the CCD is used as an array of photodetectors wherein each pixel or group of pixels corresponds to a reaction chamber rather than being used to produce an image of the array. Thus, the optics may be altered such that image quality is reduced or defocused to increase the depth of field of the optical system to collect more light from each reaction chamber. In some embodiments, it is useful to employ high aspect ratio, or columnar chambers, to concentrate the sample to be interrogated by the detector along the optical axis of the optical system, and preferably by defocussing the image to increase the depth of field. Use of a low NA lens system, preferably a bilaterally symmetrical lens system is used. It is also useful to use a detector device, for example, one or more CCD devices, having a size of, or larger than, the area of the microfluidic device to be imaged. Used in conjunction with the low NA optics, improved detection sensitivity can be realized.

A detector system can include a light source for stimulating a reporter that generates a detectable signal. The type of light source utilized depends in part on the nature of the reporter being activated. Suitable light sources include, but are not limited to, lasers, laser diodes, white light sources, and high intensity lamps. If a laser is utilized, the laser can be utilized to scan across a set of detection sections or a single detection section. Laser diodes can be microfabricated into the microfluidic device itself. Alternatively, laser diodes can be fabricated into another device that is placed adjacent to the microfluidic device being utilized to conduct a thermal cycling reaction such that the laser light from the diode is directed into the detection section.

Detection can involve a number of non-optical approaches as well. For example, the detector can also include, for example, a temperature sensor, a conductivity sensor, a potentiometric sensor (e.g., pH electrode) and/or an amperometric sensor (e.g., to monitor oxidation and reduction reactions).

Certain intercalation dyes that that have dramatic fluorescent enhancement upon binding to double-stranded DNA, and/or show strong chemical affinity for double-stranded DNA, can be used to detect double-stranded amplified DNA. Examples of suitable dyes include, but are not limited to, SYBR™ and Pico Green (from Molecular Probes, Inc. of Eugene, Oreg.), ethidium bromide, propidium iodide, chromomycin, acridine orange, Hoechst 33258, Toto-1, Yoyo-1, and DAPI (4',6-diamidino-2-phenylindole hydrochloride). Additional discussion regarding the use of intercalation dyes is provided by Zhu et al., *Anal Chem.* 66:1941-1948 (1994), which is incorporated by reference in its entirety.

As illustrated in FIG. 12, some embodiments of the present invention provide a 1:1 imaging system adapted to generate and detect fluorescent, chemiluminescent, bioluminescent, and other signals from the microfluidic device. A 1:1 imaging system is provided in some embodiments that utilizes an image detection device as large as the sample to be imaged. By providing 1:1 imaging of a large field of view, on the order of several $cm^2$, embodiments of the present invention provide increased numerical aperture (NA) optical systems. Because light collection efficiency is approximately proportional to NA², the increase in NA provided by some embodiments of the present invention enable the collection of suitable fluorescent signals from reaction chambers comprising reaction volumes on the order of one to tens of nanoliters and active fluorophore concentrations on the order of 1.0 nanoMolar. In other embodiments, active fluorophore concentrations in picoMolar ranges provide suitable fluorescent signals.

Additionally, embodiments of the present invention provide for imaging systems that are slightly reducing, forming, for example, an image that ranges from about the same size as the object to about half the object size. For example, in an embodiment, an image of a spatial region of a microfluidic device is transmitted and captured, the spatial region being associated with more than 96 chambers. An image detecting device is used to capture the image of the spatial region using an image detection spatial region that is about equal to or slightly less in size than the spatial region of the microfluidic device. Merely by way of example, the ratio of the area of the spatial region of the microfluidic device to the area of the image of the spatial region can be 1:1, 1:0.99, 1:0.95, 1:0.9, 1:0.88, and 1:0.85. These particular ratios are merely exemplary, as the ratio selected for the imaging system will depend on the particular application.

In some embodiments, the optical imaging system includes a field of view of about 3 cm×3 cm. In other embodiments, the optical imaging system includes a field of view that ranges from about 1 cm×1 cm to about 5 cm×5 cm. In particular embodiments, an object field of view of 2 cm×2 cm, 2.5 cm×2.5 cm, 2.76 cm×2.76 cm, 3.07 cm×3.07 cm, 3.5 cm×3.5 cm, and 4 cm×4 cm, is provided. In general, the field of view of the optical imaging system is selected to correspond to the spatial region of the microfluidic device, for example, an area including a number of reaction chambers of interest.

Moreover, embodiments of the present invention provide optical imaging systems with a range of numerical apertures. As an example, an NA ranging from 0.1 to 0.5 is provided according to various embodiments. In a particular embodiment, NAs of 0.15, 0.18, 0.2, 0.23, 0.25, 0.3, 0.36, and 0.4 are provided.

The spatial resolution of the optical imaging system will generally be a function of the size of the pixels in the image detecting device. In some embodiments of the present invention, the magnification (equal to one for some embodiments) and the size of the pixels present in the detector will determine the number of pixels associated with each reaction chamber. Generally, it is preferable to have multiple detector pixels associated with each reaction chamber. For example, if a reaction chamber is 45 μm on a side, up to nine square pixels having a side dimension equal to 15 μm will overlap with the reaction chamber in the 1:1 imaging system. Thus, according to embodiments of the present invention, the number of pixels associated with each reaction chamber ranges from 1 to 100. For example, 4 pixel regions, 9 pixel regions, 16 pixel regions, 25 pixel regions, 36 pixel regions, 49 pixel regions, 64 pixel regions, and 81 pixel regions are associated with each reaction chamber according to some embodiments of the present invention.

In embodiments of the present invention, a range of pixel sizes from 1 μm² to 900 μm² are utilized. For example, square pixels 1 μm on a side, 2 μm on a side, 3 μm on a side, 4 μm on a side, 5 μm on a side, 10 μm on a side, 13.5 μm on a side, 15 μm on a side, 20 μm on a side, 25 μm on a side, and 30 μm on a side are utilized in various embodiments of the present invention. As will be evident to one of skill in the art, the pixel size, the detector array dimensions, and the number of pixels per array are related. In alternative embodiments, rectangular pixels with pixel areas ranging from 1 μm² to 900 μm² are utilized.

Moreover, detector arrays, also referred to as image detecting devices, including a range of pixel counts are utilized according to various embodiments of the present invention. Array dimensions range from 512×512 pixel regions to 3,000×3,000 pixel regions. Depending on the availability of detector arrays, greater numbers of pixels per array may be provided in some embodiments. In particular embodiments, array dimensions of 1,024×1,024 pixel regions and 2,048 by 2,048 pixel regions are utilized.

Embodiments of the present invention provide an optical imaging system characterized by several system parameters. For example, a working distance of greater than 35 mm, for instance, 45.92 mm is available through embodiments of the present invention. In another embodiment, a Root-Mean-Square (RMS) spot diameter averaging 13.44 μm with a maximum value of 17.85 μm is provided. Moreover, through embodiments of the present invention, an illumination variation of about ±5% is achieved. In some embodiments, the overall length of the optical imaging system is 542.1 mm with a maximum filter AOI of 12.56 degrees, a maximum beam diameter at the filter of 76 mm, a distortion of <0.10%, and a maximum lens diameter of 5.512 inches. Additional description related to the BioMark™ system is provided in U.S. Pat. No. 7,307,802, entitled "Optical Lens System and Method for Microfluidic Devices," issued on Dec. 11, 2007, which is hereby incorporated by reference in its entirety for all purposes.

While the present invention has been described with respect to particular embodiments and specific examples thereof, it should be understood that other embodiments may fall within the spirit and scope of the invention. The scope of the invention should, therefore, be determined with reference to the appended claims along with their full scope of equivalents.

What is claimed is:

1. A method of distinguishing between a first sample with a first number of copies of a target gene and a second sample with a second number of copies of the target gene, the method comprising:
    providing a processor;
    storing a number (C) of a plurality of reaction sites in a memory;
    distributing the first sample and a reference gene among reaction sites of a first test panel having the number (C) of reaction sites;
    distributing the second sample and the reference gene among reaction sites of a second test panel having the number (C) of reaction sites;
    performing a PCR process to amplify the first sample, the second sample, and the reference gene;
    obtaining a first fluorescent image of the first test panel associated with the first sample and a first fluorescent reference image of the first test panel associated with the reference gene;
    a second fluorescent image of the second test panel associated with the second sample and a second fluorescent image of the second test panel associated with the reference gene;
    determining, using the first fluorescent image and the first fluorescent reference image, a first number ($H_1$) of the plurality of reaction sites characterized by a presence of one or more of the first sample;
    determining, using the fluorescent second image and the second fluorescent reference image, a second number ($H_2$) of the plurality of reaction sites characterized by a presence of one or more of the second sample;

computing, using the processor, a first portion ($P_1=H_1/C$) and a second portion ($P_2=H_2/C$) of the plurality of reaction sites characterized by the presence of the one or more of the first sample and the second sample, respectively:

estimating, using the processor, the first concentration ($\lambda_1$) of the first sample and a second concentration ($\lambda_2$) of the second sample as a function of the first portion and the second portion, respectively;

computing, using the processor, a first confidence interval for the estimated concentration of the first sample and a second confidence interval for the estimated concentration of the second sample;

determining that the first confidence interval and the second confidence interval do not overlap; and distinguishing between the first sample with the first number of copies of the target gene and the second sample with the second number of copies of the target gene as a result of the non-overlap of the first confidence interval and the second confidence interval.

2. The method of claim 1 wherein computing the first and second confidence intervals comprises:
computing, using the processor, a lower bound as a function of the first and second portions of the plurality of reaction sites and a standard deviation; and
computing, using the processor, an upper bound as a function of the first and second portions of the plurality of reaction sites and the standard deviation.

3. The method of claim 1 further comprising:
computing, for the first sample, a mean concentration ratio between the target gene and the reference gene; and
computing, for the second sample, a mean concentration ratio between the target gene and the reference gene.

4. The method of claim 3 wherein the first sample and the second sample are different from the reference gene.

5. The method of claim 1 wherein the plurality of reaction sites comprise a plurality of reaction chambers of a nanofluidic chip.

6. The method of claim 5 wherein the plurality of reaction sites comprise at least 765 reaction chambers in fluidic isolation.

7. The method of claim 1 wherein the plurality of reaction sites comprise a plurality of droplets.

8. The method of claim 1 wherein $\lambda_1=-\ln(1-P_1)$ and $\lambda_2=-\ln(1-P_2)$.

9. A method of estimating a ratio of a concentration of a first DNA molecule with a first number of copies of a target gene in a biological sample to a concentration of a second DNA molecule with a second number of copies of a target gene in the biological sample, the method comprising:
providing a processor;
storing a number (C) of a plurality of reaction sites in a memory;
distributing the biological sample and a reference gene among the plurality of reaction sites;
performing a PCR process to amplify the first DNA molecules, the second DNA molecules, and the reference gene;
capturing a first fluorescent image of the plurality of reaction sites associated with the first DNA molecule and a second fluorescent reference image associated with the reference gene;
capturing a second fluorescent image of the plurality of reaction sites associated with the second DNA molecule and a second fluorescent reference image associated with the reference gene;
determining, using the first fluorescent image and the first fluorescent reference image, a first number ($H_1$) of the plurality of reaction sites characterized by a presence of one or more of the first DNA molecules;
determining, using the second fluorescent image and the second fluorescent reference image, a second number ($H_2$) of the plurality of reaction sites characterized by a presence of one or more of the second DNA molecules;
computing, using the processor, a first portion ($P_1=H_1/C$) of the plurality of reaction sites characterized by the presence of the one or more first DNA molecules based on:
the stored number of the plurality of reaction sites; and
the first number of the plurality of reaction sites characterized by the presence of one or more of the DNA molecules;
computing, using the processor, a second portion ($P_2=H_2/C$) of the plurality of reaction sites characterized by the presence of the one or more second DNA molecules based on:
the stored number of the plurality of reaction sites; and
the second number of the plurality of reaction sites characterized by the presence of one or more of the DNA molecules;
estimating, using the processor, the concentration ($\lambda_1$) of the first DNA molecule as a function of the first portion of the plurality of reaction sites;
estimating, using the processor, the concentration ($\lambda_2$) of the second DNA molecule as a function of the second portion of the plurality of reaction sites;
computing a first confidence interval for the concentration of the first DNA molecule and a second confidence interval for the concentration of the second DNA molecule;
determining that the first confidence interval and the second confidence interval do not overlap; and
computing, using the processor, the ratio of the concentration of the first DNA molecule in the biological sample to the concentration of a second DNA molecule in the biological sample.

10. The method of claim 9 further comprising:
computing a mean concentration ratio between the first DNA molecule and the reference gene; and
computing a mean concentration ratio between the second DNA molecule and the reference gene.

11. The method of claim 9 wherein the plurality of reaction sites comprise a plurality of reaction chambers of a nanofluidic chip.

12. The method of claim 11 wherein the plurality of reaction sites comprise at least 765 reaction chambers in fluidic isolation.

13. The method of claim 9 wherein $\lambda_1=-\ln(1-P_1)$.

14. The method of claim 9 wherein $\lambda_2=-\ln(1-P_2)$.

* * * * *